(12) United States Patent
Ueda

(10) Patent No.: US 9,259,487 B2
(45) Date of Patent: Feb. 16, 2016

(54) TRANSGENIC NON-HUMAN ANIMAL MODEL OF NEURODEGENERATIVE DISEASE

(75) Inventor: Hiroshi Ueda, Nagasaki (JP)

(73) Assignee: Nagasaki University, Nagasaki (JP)

( * ) Notice: Subject to any disclaimer, the term of this patent is extended or adjusted under 35 U.S.C. 154(b) by 39 days.

(21) Appl. No.: 14/122,522

(22) PCT Filed: May 18, 2012

(86) PCT No.: PCT/JP2012/062776
§ 371 (c)(1),
(2), (4) Date: Jan. 7, 2014

(87) PCT Pub. No.: WO2012/165175
PCT Pub. Date: Dec. 6, 2012

(65) Prior Publication Data
US 2014/0130190 A1 May 8, 2014

(30) Foreign Application Priority Data

May 27, 2011 (JP) .................. 2011-119651
Feb. 9, 2012 (JP) .................. 2012-026636

(51) Int. Cl.
| | |
|---|---|
| A01K 67/00 | (2006.01) |
| A01K 67/027 | (2006.01) |
| C07H 21/04 | (2006.01) |
| G01N 33/00 | (2006.01) |
| A61K 49/00 | (2006.01) |
| C07K 14/575 | (2006.01) |
| C12N 15/85 | (2006.01) |

(52) U.S. Cl.
CPC ......... *A61K 49/0008* (2013.01); *A01K 67/0276* (2013.01); *C07K 14/57581* (2013.01); *C12N 15/8509* (2013.01); *A01K 67/027* (2013.01); *A01K 2217/075* (2013.01); *A01K 2217/206* (2013.01); *A01K 2227/105* (2013.01); *A01K 2267/0318* (2013.01); *C07H 21/04* (2013.01); *C12N 2800/30* (2013.01)

(58) Field of Classification Search
CPC ............ A01K 67/027; A01K 67/0276; A01K 2227/105; A01K 2267/0318; A01K 49/0008; C07H 21/04
USPC ............................ 800/3, 9, 18; 536/23.2, 24.1
See application file for complete search history.

(56) References Cited

FOREIGN PATENT DOCUMENTS

WO WO 2004/064861 A1 8/2004
WO WO 2011/019023 A1 2/2011

OTHER PUBLICATIONS

Houdebine, L-M., 2002, Journal of Biotechnology, vol. 98, p. 145-160.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Iannicola et al., 2000, Journal of Neurochemistry, vol. 75, p. 830-839.*
Tallaksen-Greene et al., 2011, Neuropsychopharmacology, vol. 36, p. 2373-2374.*
Bonelli et al., *Current Pharmaceutical Design*, 12(21): 2701-2720 (2006).
Fujita et al., *Cell Death and Differentiation*, 14: 1839-1842 (2004).
Gaveriaux-Ruff et al., *Pharmacology & Therapeutics*, 113(3): 619-634 (2007).
Iannicola et al., *Journal of Neurochemistry*, 75(2): 830-839 (2002).
Kelly et al., *Biochem. Soc. Trans.*, 37: 323-328 (2009).
Kishioka et al., PLoS ONE, 4(1): e4157 (2009).
Lang et al., *The New England Journal of Medicine*, 339(16): 1130-1143 (1998).
Mangiarini et al., *Cell*, 87(1): 493-506 (1996).
Menalled et al., *The Journal of Comparative Neurology*, 465: 11-26 (2003).
Nishiyama, Nobuyoshi, "Shinkei Saiboshi ni Okeru Saibo Shuki Saishinko no Kan'yo", *Brain 21*, 11(3): 38-43 (2008).
Segawa, Masaya, *Brain & Development*, 33: 195-201 (2011).
Slow et al., *Human Molecular Genetics*, 12(13): 1555-1567 (2003).
Walker, Francis O., *Lancet*, 369: 218-228 (2007).
Japanese Patent Office, International Search Report in International Patent Application No. PCT/JP2012/062776 (Aug. 21, 2012).
Nishiyama, Nobuyoshi, "Shinkei Saiboshi ni Okeru Saibo Shuki Saishinko no Kan'yo" ["Involvement of Cell Cycle Reactivation in Neuronal Cell Death"], *Brain 21*, 11(3): 38-43 (2008).

* cited by examiner

*Primary Examiner* — Shin Lin Chen
(74) *Attorney, Agent, or Firm* — Leydig, Voit & Mayer, Ltd.

(57) ABSTRACT

The present invention provides a non-human mammal deficient in the expression of prothymosin α gene in the striatum and a screening method for a prophylactic/therapeutic drug for Huntington's disease and the like, which uses the animal.

17 Claims, 15 Drawing Sheets

1: Gng7-cre primer PCR
  WT band 495bp
  MT band 570bp

2: ProTα$^{flox/flox}$ primer PCR
  WT band 304bp
  MT band 363bp

TRANSGENIC NON-HUMAN ANIMAL MODEL OF NEURODEGENERATIVE DISEASE

CROSS-REFERENCE TO RELATED APPLICATIONS

This patent application is the U.S. national phase of International Patent Application No. PCT/JP2012/062776, filed on May 18, 2012, which claims the benefit of Japanese Patent Application No. 2011/119651, filed on May 27, 2011, and Japanese Patent Application No. 2012/026636, filed on Feb. 9, 2012, each of which is incorporated by reference in its entirety herein.

INCORPORATION-BY-REFERENCE OF MATERIAL ELECTRONICALLY SUBMITTED

Incorporated by reference in tis entirety herein is a computer-readable nucletide/amino acid sequence listing submitted concurrently herewith and identified as follows: 1,219 bytes ASCII (Text) filed named "715703SequenceListing.txt," created Nov. 26, 2013.

TECHNICAL FIELD

The present invention relates to a non-human mammal deficient in the expression of prothymosin α gene in the striatum and the like.

BACKGROUND ART

Neurodegenerative diseases caused by denaturation and falling off of nerve cells of the central nervous system are known to accompany injury of a particular site for each disease. Among them are Parkinson's disease and Huntington's disease wherein nerve cells of the basal nucleus, which is a major constituent region of the extrapyramidal tract that controls and regulates the motility function, are injured. The former is caused by denaturation of dopaminergic neuron that projects from the substantia nigra pars *compacta* to the striatum (non-patent document 1), and the latter is caused by denaturation of GABAergic neuron that projects from the striatum to the globus pallidus and substantia nigra pars *reticulata* (non-patent document 2). The both are designated as the object of specific disease treatment research program as diseases with high refractory nature and high severity, and further clarification of the cause and the development of a therapeutic drug are expected. Huntington's disease is a dominantly-inherited disease which is developed in a little under 1 in 10,000 Caucasians and up to 1 in several 10,000 people of other races. Particularly the symptoms become serious when a causative gene derived from a father is present. The symptoms thereof include motor symptoms called dystonia such as abnormal involuntary movements and abnormal posture, as well as psychological symptoms such as depression, dementia and the like. While the development of a new drug for Huntington's disease has been tried and plural candidate substances have been recited; however, effectiveness has not been established to date (non-patent document 3).

Of the symptoms of Huntington's disease, L-DOPA preparations have been empirically administered for dystonia (non-patent document 4). Although L-DOPA preparation shows superior effectiveness, it shows a short duration of action, effect variation (wearing off, on-off) and symptoms of dyskinesia and the like due to a long-term use, thus degrading the patients' QOL. Therefore, dopamine agonist providing an effect next to L-DOPA preparation and having a long duration of action has been drawing attention. At present, 6 kinds of dopamine agonists are clinically used in Japan. Particularly, pramipexole is reported to show a treatment effect for myotonia in the Huntington's disease (non-patent document 5), and establishment of the effectiveness is expected.

Under the circumstances, several Huntington's disease-like animal models have been established for the evaluation of and screening for a therapeutic drug for Huntington's disease. The initially reported Huntington's disease-like model mouse is R6/2 mouse introduced with exon1 of Huntington's disease gene that the patients with Huntington's disease have. Although nerve cell death is not observed, symptoms of a decrease in the brain weight, a low muscle amount, an increase in the amount of calorie intake, an increase in the urination frequency, drastic shortening of life span, clasping, tremor and the like have been reported (non-patent document 6). However, since Huntington's disease-like animal models die at the age of 10-12 weeks on average, a long-term study of drug effect is difficult. Moreover, since the symptoms thereof are wide-ranging and go beyond the motor disorder, specific functional analysis is problematically difficult. As a model mouse developed to solve all these problems, which does not induce nerve cell death, a knock-in mouse having a CAG repeat sequence obtained from human Huntington's disease patients has been reported (non-patent documents 7, 8). However, there is an increasing need for a model suitable for the study of a new drug aiming to improve motor symptoms.

DOCUMENT LIST

Non-patent Documents non-patent document 1: Lang, A. E. and A. M. Lozano, Parkinson's disease. Second of two parts. N Engl J Med, 1998. 339(16): p. 1130-43.

non-patent document 2: Kelly, C. M., S. B. Dunnett, and A. E. Rosser, Medium spiny neurons for transplantation in Huntington's disease. Biochem Soc Trans, 2009. 37(Pt1): p. 323-8.

non-patent document 3: Walker, F. O., Huntington's disease. Lancet, 2007.369 (9557): p. 218-28.

non-patent document 4: Segawa, M., Hereditary progressive dystonia with marked diurnal fluctuation. Brain Dev.

non-patent document 5: Bonelli, R. M. and G. K. Wenning, Pharmacological management of Huntington's disease: an evidence-based review. Curr Pharm Des, 2006. 12(21): p. 2701-20.

non-patent document 6: Laura Mangiarini et al., Cell, Vol. 87, 1996: p. 493-506.

non-patent document 7: Liliana B. Menalled et al., The Journal of Comparative Neurology, Vol. 465, 2003: p. 11-26.

non-patent document 8: Elizabeth J. Slow et al., Human Molecular Genetics, Vol. 12, No. 13, 2003: p. 1555-1567.

SUMMARY OF THE INVENTION

Problems to be Solved by the Invention

An object of the present invention is to provide a non-human mammal deficient in the expression of prothymosin α gene in the striatum and a screening method for a prophylactic/therapeutic drug for neurodegenerative diseases including Huntington's disease, which uses the animal.

Means of Solving the Problems

The present inventors previously found prothymosin α as a nuclear protein that suppresses neurotic necrotic cell death induced by an ischemia stress (Ueda H et al., J Cell Biol. Vol. 176(6), 853-862, 2007). Thus, the present inventors generated a conditional knockout mouse deficient in the expression of prothymosin α in the striatum by linking a cre protein gene to the downstream of a G protein γ7 subunit gene (Gng7) promoter that expresses striatum—specifically in the striatum GABA neuron having an excitatory dopamine receptor, while utilizing the cre-loxP system. The mouse lacks functional prothymosin α in the striatum GABA neuron, and has lost a neuroprotective action under an ischemia stress. The present inventors have evaluated the phenotype of the mouse young in the weeks of age under ischemia produced by a treatment, and studied the effects of pramipexole (dopamine D2 receptor agonist) and selegiline (dopamine metabolism inhibitor) on the mouse. As a result, the mouse was confirmed to have the features found in known Huntington's disease model mouse. In addition, they have found that the symptoms thereof can be improved by the administration of a dopamine D2 receptor agonist, a dopamine metabolism inhibitor or an NMDA receptor antagonist. Furthermore, the present inventors have also evaluated the phenotype of the mouse with weeks of age and studied the effects of a dopamine D1 receptor agonist, SKF38393. As a result, it has been found that symptoms similar to ischemia produced by a treatment are naturally developed by aging and the symptoms can be improved by a dopamine D1 receptor agonist.

The present inventors have conducted further studies based on these findings and completed the present invention.

Accordingly, the present invention provides

[1] A non-human mammal deficient in the expression of prothymosin α gene in the striatum, which, as compared to a corresponding wild-type animal,
(1) is vulnerable to cerebral ischemia produced by a treatment,
(2) is inferior in motility,
(3) spontaneously develops the conditions of the above-mentioned (1) and (2) by aging, and
(4) shows improve symptoms of the above-mentioned (1), (2) and (3) by a dopamine D2 receptor agonist, a dopamine metabolism inhibitor, an NMDA receptor antagonist or a dopamine D1 receptor agonist;

[2] the animal of the above-mentioned [1], which has a cre gene showing expression regulated by a G protein γ7 subunit gene promoter, and a homozygous prothymosin α gene flanked with loxP sequences;

[3] the animal of the above-mentioned [1], wherein the dopamine D2 receptor agonist is pramipexole, pergolide, cabergoline, is talipexole or ropinirole;

[4] the animal of the above-mentioned [1], wherein the dopamine metabolism inhibitor is selegiline, entacapone, amantadine, L-DOPA, droxidopa or zonisamide;

[5] the animal of the above-mentioned [1], wherein the NMDA receptor antagonist is memantine or CP-101606;

[6] the animal of the above-mentioned [1], wherein the dopamine D1 receptor agonist is SKF38393;

[7] the animal of the above-mentioned [1], wherein the animal is mouse or rat;

[8] a screening method for a therapeutic/prophylactic drug for a neurodegenerative disease or dystonia derived from an ischemic disease, comprising applying a test compound to the animal of the above-mentioned [1], and measuring (1) a survival ratio in a cerebral ischemia produced by a treatment and/or (2) motility;

[9] a screening method for a therapeutic/prophylactic drug for a neurodegenerative disease or dystonia derived from an ischemic disease, comprising applying a test compound to the animal of the above-mentioned [1] and with age, and measuring
(1) a survival ratio and/or (2) motility;

[10] the screening method of the above-mentioned [8] or [9], wherein the test compound is a dopamine D2 receptor agonist;

[11] the screening method of the above-mentioned [8] or [9], wherein the test compound is a dopamine metabolism inhibitor;

[12] the screening method of the above-mentioned [8] or [9], wherein the test compound is an NMDA receptor antagonist;

[13] the screening method of the above-mentioned [8] or [9], wherein the test compound is a dopamine D1 receptor agonist;

[14] the screening method of the above-mentioned [8] or [9], wherein the neurodegenerative disease is Huntington's disease; and the like.

Effect of the Invention

According to the non-human mammal deficient in the expression of prothymosin α gene in the striatum of the present invention, a novel prophylactic/therapeutic drug for neurodegenerative diseases including Huntington's disease can be screened for.

DESCRIPTION OF EMBODIMENTS

Figure 1:
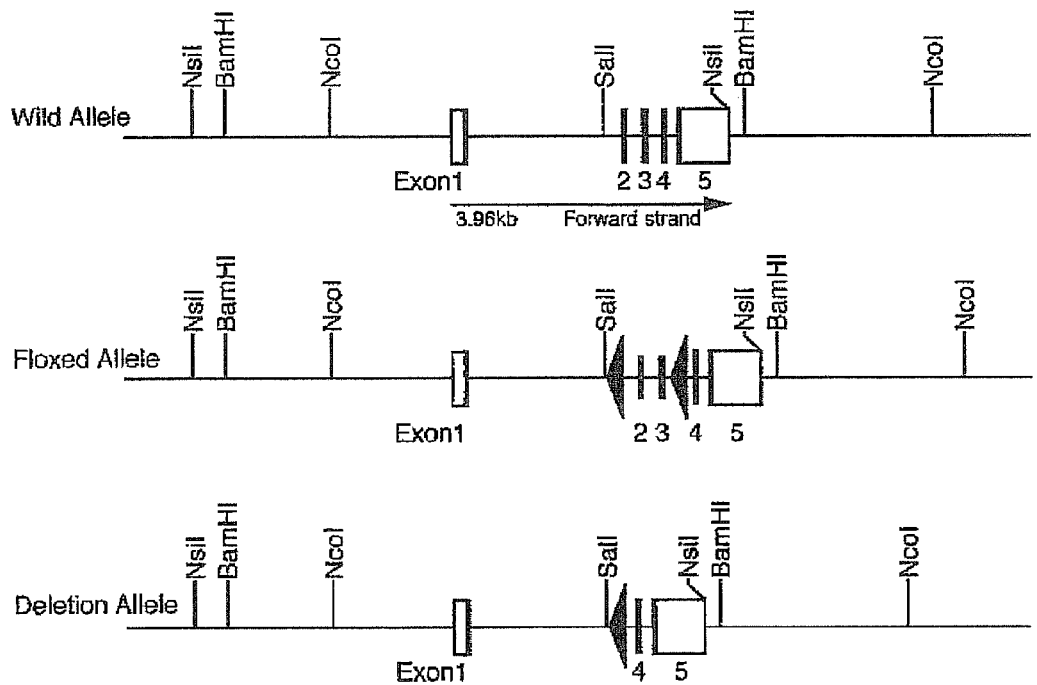
FIG. 1 shows the structures of wild-type allele, Floxed allele and defective allele of mouse prothymosin α gene.

The present invention provides a non-human mammal deficient in the expression of the prothymosin α gene in striatum.

The non-human mammal deficient in the expression of prothymosin α gene in the striatum means a non-human mammal wherein expression of endogenous prothymosin α is inactivated in the striatum. Examples thereof include non-human mammal wherein prothymosin α gene in the striatum is knocked out, which is obtained by crossing a prothymosin α gene-modified non-human mammal prepared from a recombinant ES cell having a prothymosin α gene flanked with loxP sequences and a genetically-modified non-human mammal having a cre gene expressed striatum—specifically, a knocked down (KD) non-human mammal wherein expression of a prothymosin α gene is inactivated in the striatum by antisense or RNAi technique, and the like. Here, "knocked out (KO)" means that the production of complete mRNA is prevented by destroying or removing the endogenous gene, whereas "knocked down (KD)" means that translation from mRNA into protein is inhibited to inactivate the expression of the endogenous gene. Hereinafter, the striatum prothymosin α gene KO/KD animal in the present invention is sometimes simply referred to as "the KO/KD animal of the present invention". Moreover, being inactivated in the striatum means that the gene expression of prothymosin α is inactivated in the striatum which is a part of the basal nucleus, and a significant difference is not found in the expression of the gene in a wild-type non-human mammal and tissues other than the striatum.

"A non-human mammal" that can be a subject of the present invention is not particularly limited, as long as it is a non-human mammal for which a transgenic system has been established; examples include mice, rats, bovines, monkeys, pigs, sheep, goat, rabbits, dogs, cats, guinea pigs, hamsters and the like. Mice, rats, rabbits, dogs, cats, guinea pigs, hamsters and the like are preferable; in particular, from the viewpoint of the preparation of disease model animals, rodents, which have relatively short periods of ontogeny and life cycles, and which are easy to propagate, are more preferable; particularly, mice (e.g., C57BL/6 strain, BALB/c strain, DBA2 strain and the like as pure strains, B6C3$F_1$ strain, $BDF_1$ strain, $B6D2F_1$ strain, ICR strain and the like as hybrid strains) and rats (e.g., Wistar, SD and the like) are preferable.

In addition to mammals, birds such as chickens can be used for the same purpose as that of "non-human mammals" being subjects of the present invention.

As a specific means for knocking out a prothymosin α gene in the striatum, a method including incorporating a DNA strand having a DNA sequence constructed to consequently inactivate the gene, by isolating a prothymosin α gene (genome DNA) derived from a target non-human mammal by a conventional method, cleaving out the whole or a part of the prothymosin α gene using, for example, the Cre-loxP system or Flp-frt system to delete the gene (hereinafter to be abbreviated as targeting vector) into the prothymosin α gene locus of the target non-human mammal by homologous recombination and the like can be preferably used.

The homologous recombinant can be acquired by, for example, introducing the above-described targeting vector into an embryonic stem cell (ES cell).

An ES cell refers to a cell derived from an inner cell mass (ICM) of a fertilized egg in the blastocyst stage, and can be cultivated and maintained while keeping the undifferentiated state in vitro. ICM cells are destined to form the embryo body, being stem cells on which all tissues, including germ cells, are based. The ES cell used may be of an established cell line, is or of a cell line newly established in accordance with the method of Evans and Kaufman (Nature, vol. 292, p. 154, 1981). For example, in the case of mouse ES cells, ES cells derived from a 129 mouse strain are currently generally used, but the immunological background thereof is unclear; for the purposes of acquiring ES cells of a pure strain instead thereof with an immunologically clear genetic background and the like, an ES cell established from a C57BL/6 mouse or from a $BDF_1$ mouse ($F_1$ of C57BL/6 and DBA/2), wherein the small number of ova collectable from C57BL/6 has been improved by crossing with DBA/2, and the like can also be used suitably. In addition to being advantageous in that the number of ova collectable is high, and that the ova are robust, $BDF_1$ mice have the C57BL/6 mouse as the background thereof; therefore, ES cells derived therefrom can be used advantageously in that, when preparing a disease model mouse, the genetic background can be replaced with that of the C57BL/6 mouse by back-crossing with a C57BL/6 mouse.

ES cells can be prepared, for example, as described below. When a blastocystic embryo is collected from the uterus of a female non-human mammal after mating [for example, when a mouse (preferably a mouse of an inbred strain such as C57BL/6J(B6), $F_1$ of B6 and another inbred strain, and the like) is used, a female mouse at about 8 to about 10 week-old (about 3.5 days of gestation) mated with a male mouse at about 2 month-old or more is preferably used] (or an early embryo in the morula stage or before is collected from the oviduct, after which it may be cultured in a medium for embryo culture as described above until the blastocyst stage), and cultured on a layer of appropriate feeder cells (e.g., in the case of a mouse, primary fibroblasts prepared from a fetal mouse, commonly known STO fibroblast line and the like), some cells of the blastocyst gather to form an ICM that will differentiate into an embryo. This inner cell mass is trypsinized to dissociate single cells, and while maintaining an appropriate cell density and making medium exchanges, dissociation and passage are repeated, whereby ES cells are obtained.

Although both male and female ES cells can be used, male ES cells are usually more convenient in preparing a germline chimera. Also for the sake of saving painstaking labor for cultivation, it is desirable that sex identification be performed as early as possible. An example of the method of identifying the sex of an ES cell is a method comprising amplifying and detecting a gene in the sex determining region on Y chromosome by PCR. Using this method, about 1 colony of ES cells (about 50 cells) is sufficient, compared with the conventional method, which requires about $10^6$ cells for karyotype analysis, so that primary selection of ES cells in early stages of cultivation can be performed by sex identification, thus making early selection of male cells possible, whereby labor in early stages of cultivation can be reduced significantly.

Secondary selection can be performed by, for example, confirming chromosome numbers by the G-banding method, and the like. It is desirable that the chromosome number of the ES cell obtained be 100% of the normal number.

The ES cell line thus obtained needs to be subcultured carefully to maintain the nature of undifferentiated stem cells. For example, the ES cell line is cultured by, for example, a method comprising culturing on appropriate feeder cells, like STO fibroblasts, in the presence of LIF (1 to 10,000 U/ml), known as a differentiation suppressing factor, in a gaseous carbon dioxide incubator (preferably, 5% gaseous carbon dioxide/95% air or 5% oxygen/5% gaseous carbon dioxide/90% air) at about 37° C., and the like; upon passage, for example, the ES cell line is treated with trypsin/EDTA solution (usually 0.001 to 0.5% trypsin/0.1 to 5 mM EDTA, preferably about 0.1% trypsin/1 mM EDTA) to obtain single cells, which are sown onto freshly prepared feeder cells, and the like. This passage is normally performed every 1 to 3 days, during which the cells were examined; if a morphologically abnormal cell is found, it is desirable that the cultured cells be discarded.

ES cells can be differentiated into a wide variety of types of cell, including parietal muscle, visceral muscles, and cardiac muscle, by monolayer culture until the reach of a high density, or suspension culture until the formation of cell aggregates, under appropriate conditions [M. J. Evans and M. H. Kaufman, Nature vol. 292, p. 154, 1981; G. R. Martin, Proceedings of the National Academy of Sciences, USA (Proc. Natl. Acad. Sci. U.S.A.), vol. 78, p. 7634, 1981; T. C. Doetschman et al., Journal of Embryology and Experimental Morphology, vol. 87, p. 27, 1985].

For example, when the targeting vector is designed to cut out the whole or a part of the prothymosin α gene using the Cre-loxP system to delete the gene, the vector can assume, for example, the constitution shown below.

First, for a DNA fragment containing the whole or a part of the modified prothymosin α gene into the whole or a part of the endogenous prothymosin α gene to be inserted by homologous recombination, the targeting vector needs to contain sequences homologous to the respective target sites (5' arm and 3' arm) at the upstream of the 5' and downstream of the 3' in the DNA fragment containing the whole or a part of the modified prothymosin α gene (e.g., targeting vector contains a sequence homologous to the 5' regulatory region of the prothymosin α gene at the upstream of the 5' of the other DNA fragment inserted, and a sequence homologous to the 3' untranslated region of the prothymosin α gene at the 3' downstream thereof).

The prothymosin α gene in the present invention is specifically a DNA containing a base sequence, which is the same as or substantially the same as the base sequence registered as GenBank accession No. NM_008972.2, when the target non-human mammal is a mouse. When the target non-human mammal is a rat, a DNA containing a base sequence the same as or substantially the same as the base sequence registered as GenBank accession No. NM_021740.1 can be mentioned.

The base sequence, which is substantially the same as the base sequence of prothymosin α gene, is, for example, a base sequence having an identity of about 70% or more, preferably about 80% or more, more preferably about 90% or more, most preferably about 95% or more, to the base sequence. The base sequence identity herein can, for example, be calculated using the homology calculation algorithm NCBI BLAST (National Center for Biotechnology Information Basic Local Alignment Search Tool) under the following conditions (expect=10; gap allowed; filtering=ON; match score=1; mismatch score=−3).

Moreover, the targeting vector needs to have loxP sequences in tandem such that they are located inside a sequence homologous to each target region and sandwich the whole or a part of the prothymosin α gene. In the DNA fragment incorporated on the chromosome by homologous recombination, Cre protein acts on the loxP sequences at the 5' side and 3' side of the whole or a part of the prothymosin α gene, whereby the whole or a part of the prothymosin α gene flanked with the loxP sequences is cut out and the prothymosin α gene is knocked out.

Although the other DNA fragment inserted is not particularly limited, it is possible to select ES cells having a targeting vector integrated in a chromosome thereof with drug resistance or reporter activity as the index, by using a drug resistance gene or a reporter gene. Here, examples of the drug resistance gene and examples of the reporter gene include, but are not limited to, the neomycin phosphotransferase II (nptII) gene, the hygromycin phosphotransferase (hpt) gene and the like, and the β-galactosidase (lacZ) gene, the chloramphenicol acetyltransferase (cat) gene and the like, respectively.

The drug resistance or reporter gene is preferably under the control of an optionally chosen promoter capable of functioning in mammalian cells. For example, virus promoters such as the SV40 early promoter, cytomegalovirus (CMV) long terminal repeat (LTR), Rous sarcoma virus (RSV) LTR, mouse leukemia virus (MoMuLV) LTR, and adenovirus (AdV)-derived early promoter, and promoters for mammalian constitutive protein genes such as the β-actin gene promoter, PGK gene promoter, and transferrin gene promoter and the like can be mentioned.

The targeting vector preferably has a sequence that terminates the transcription of mRNA from the gene (polyadenylation (polyA) signal, also called terminator) downstream of the drug resistance or reporter gene; for example, terminator sequences derived from virus genes, or from various mammal or bird genes, can be used. Preferably, an SV40 terminator and the like are used.

Usually, gene recombination in a mammal occurs mostly non-homologously; the introduced DNA is randomly inserted at an optionally chosen position on the chromosome. Therefore, it is not possible to efficiently select only those clones targeted to the endogenous prothymosin α gene targeted by homologous recombination by selection based on the detection of the expression of a drug resistance or reporter gene and the like (positive selection); it is necessary to confirm the site of integration by Southern hybridization or PCR for all the clones selected. Hence, provided that, for example, the herpes simplex virus-derived thymidine kinase (HSV-tk) gene, which confers gancyclovir susceptibility, is joined outside the region homologous to the target sequence of the targeting vector, the cells having the vector inserted randomly thereinto cannot grow in a gancyclovir-containing medium because they have the HSV-tk gene, whereas the cells targeted to the endogenous prothymosin α locus by homologous recombination become resistant to gancyclovir and are selected because they do not have the HSV-tk gene (negative selection). Alternatively, provided that the diphtheria toxin gene, for example, is joined in place of the HSV-tk gene, the cells having the vector inserted randomly thereinto die due to the toxin produced by themselves, so that a homologous recombinant can also be selected in the absence of a drug.

Although any of the calcium phosphate co-precipitation method, electroporation method, lipofection method, retrovirus infection method, aggregation method, microinjection method, gene gun (particle gun) method, DEAE-dextran method and the like can be used for targeting vector introduction into ES cells, the electroporation method is generally chosen because of the ease of treatment of a large number of cells and the like, since gene recombination in a mammal occurs mostly non-homologously so that the frequency of obtainment of homologous recombinants is low, as described above. For the electroporation, ordinary conditions used for transfection into animal cells may be used as is; for example, the electroporation can be performed by trypsinizing ES cells in the logarithmic growth phase to disperse them as single cells, suspending the cells in a medium to obtain a density of $10^6$ to $10^8$ cells/ml, transferring the cells to a cuvette, adding 10 to 100 μg of a targeting vector, and applying an electric pulse of 200 to 600 V/cm.

ES cells having the targeting vector integrated therein can be determined by screening chromosomal DNA separated and extracted from a colony obtained by culturing the single cells on feeder cells, by Southern hybridization or PCR; if a drug resistance gene or a reporter gene is used as the other DNA fragment, it is possible to select a transformant at the cellular stage with the expression thereof as the index. For example, if a vector comprising the nptII gene as the marker gene for positive selection is used, ES cells after transfection treatment are cultured in a medium containing a neomycin-series antibiotic such as G418, and the resulting resistant colony is selected as a candidate for a transformant. If a vector comprising the HSV-tk gene is used as the marker gene for negative selection, the ES cells are cultured in a medium containing ganciclovir, and the resulting resistant colony is selected as a candidate for a homologous recombinant. The colonies obtained are transferred to respective culture plates, and trypsinization and medium exchanges are repeated, after which a portion is reserved for cultivation, and the remainder is subjected to PCR or Southern hybridization to confirm the presence of the introduced DNA.

When an ES cell confirmed to have the introduced DNA integrated therein is returned to an embryo derived from a non-human mammal of the same species, the ES cell gets integrated into the ICM of the host embryo to form a chimeric embryo. This is transplanted into a recipient mother (embryo recipient female) and allowed to continue development, whereby a chimeric non-human mammal having a modified prothymosin α gene is obtained. If the ES cell contributes to the formation of a primordial germ cell that will differentiate into an egg or spermatozoon in the chimeric animal, a germline chimera will be obtained; by mating this, a non-human mammal having the prothymosin α genetic modification maintained genetically therein can be prepared.

For preparing a chimeric embryo, there are a method wherein early embryos up to the morula stage are adhered and aggregated together (aggregation chimera method) and a method wherein a cell is micro-injected into a blastocoel cavity of a blastocyst (injection chimera method). Although the latter has traditionally been widely conducted in the preparation of a chimeric embryo using an ES cell, a method wherein an aggregation chimera is created by injecting an ES cell into the zona pellucida of an 8-cell stage embryo, and a method wherein an aggregation chimera is created by co-culturing and aggregating an ES cell mass and an 8-cell stage embryo deprived of the zona pellucida, as a method which does not require a micromanipulator and which can be easily operated, have recently been conducted.

In all cases, a host embryo can be collected from a non-human mammal that can be used as a female for egg collection in transfection into a fertilized egg as below mentioned in the same manner; for example, in the case of a mouse, to make it possible to determine the percent contribution of ES cells to the formation of a chimera mouse by coat color, it is preferable that the host embryo be collected from a mouse of a strain showing a coat color different from that of the strain from which the ES cell is derived. For example, in the case of an ES cell derived from a 129 mouse strain (coat color: agouti), a C57BL/6 mouse (coat color: black) or an ICR mouse (coat color: albino) is used as the female for egg collection; in the case of an ES cell derived from a C57BL/6 or $DBF_1$ mouse (coat color: black) or from a TT2 cell (derived from $F_1$ (coat color: agouti) of C57BL/6 and CBA), an ICR mouse or a BALB/c mouse (coat color: albino) can be used as the female for egg collection.

Because the germline chimera formation capacity depends largely on the combination of an ES cell and a host embryo, it is more preferable that a combination showing a high germline chimera formation capacity be chosen. For example, in the case of a mouse, it is preferable to use a host embryo derived from the C57BL/6 strain and the like for ES cells derived from the strain, and to use a host embryo derived from the BALE/c strain and the like for ES cells derived from the C57BL/6 strain.

It is preferable that the female mouse for egg collection be about 4 to about 6 week-old, and that the male mouse for mating be of the same strain at about 2 to about 8 month-old. Although the mating may be by natural mating, it is preferably performed after administering gonadotropic hormones (follicle-stimulating hormone, then luteinizing hormone) to induce overovulation.

In the case of the blastocyst injection method, a blastocystic embryo (e.g., in the case of a mouse, at about 3.5 days after mating) is collected from the uterus of a female for egg collection (or an early embryo in the morula stage or before, after being collected from the oviduct, may be cultured in a medium (below-mentioned) for embryo culture until the blastocyst stage), and ES cells (about 10 to about 15 cells) having a targeting vector introduced thereinto are injected into a blastocoel cavity of the blastocyst using a micromanipulator, after which the embryos are transplanted into the uterus of a pseudopregnant embryo recipient female non-human mammal. As the embryo recipient female non-human mammal, a non-human mammal that can be used as an embryo recipient female in transfection into a fertilized egg can be used in the same manner.

In the case of the co-culture method, 8-cell stage embryos and morulas (e.g., in the case of a mouse, about 2.5 days after mating) are collected from the oviduct and uterus of a female for egg collection (or an early embryo in the 8-cell stage or before, after being collected from the oviduct, may be cultured in a medium for embryo culture until the 8-cell stage or morula stage), and the zona pellucida is lysed in acidic Tyrode's solution, after which an ES cell mass incorporating a targeting vector (number of cells: about 10 to about 15 cells) is placed in a microdrop of a medium for embryo culture overlaid with mineral oil, the above-described 8-cell stage embryo or morula (preferably 2 embryos) is further placed, and they are co-cultured overnight. The morula or blastocyst obtained is transplanted to the uterus of an embryo recipient female non-human mammal as described above.

If the transplanted embryo implants successfully and the embryo recipient female becomes pregnant, chimeric non-human mammal pups will be obtained by natural delivery or caesarean section. Embryo recipient females that have delivered spontaneously are allowed to continue suckling; if the pups are delivered by caesarean section, the pups can be suckled by a separately provided female for suckling (a female non-human mammal with usual mating and delivery).

For the selection of a germline chimera, if the sex of the ES cell has already been determined, a chimera mouse of the same sex as the ES cell first is selected (usually, a male chimera mouse is chosen since a male ES cell is used), and then a chimera mouse showing a high ES cell contribution rate (e.g., 50% or more) is selected on the basis of phenotypes such as coat color. For example, in the case of a chimera mouse obtained from a chimera embryo between a D3 cell, which is a male ES cell derived from a 129 mouse strain, and a host embryo derived from a C57BL/6 mouse, it is preferable that a male mouse showing a high percentage of the agouti coat color be selected. Whether or not the selected chimera non-human mammal is a germline chimera can be determined on the basis of the phenotypes of the $F_1$ animal obtained by crossing with an appropriate strain of the same animal species. For example, in the case of the above-described chimera mouse, agouti is dominant over black; therefore, when the male mouse is crossed with a female C57BL/6 mouse, the coat color of the $F_1$ obtained is agouti if the selected male mouse is a germline chimera.

The thus-obtained germline chimera non-human mammal incorporating a targeting vector (founder) is usually obtained as a heterozygote having the prothymosin α gene only modified in either one of the homologous chromosomes. To obtain a homozygote having the prothymosin α gene modified in both homologous chromosomes, of the $F_1$ animals obtained as described above, siblings of heterozygotes may be crossed. Selection of heterozygotes can be determined by, for example, screening chromosomal DNAs separated and extracted from the tail of an $F_1$ animal by Southern hybridization or PCR. ¼ of the $F_2$ animals obtained will be homozygotes.

In another preferred embodiment with the use of a virus as the targeting vector, a method comprising infecting an ES cell of a non-human mammal with a virus comprising a DNA comprising a marker gene for positive selection inserted between the 5' and 3' arms, and a marker gene for negative selection outside the arms, can be mentioned (see, for example, Proceedings of the National Academy of Sciences, USA (Proc. Natl. Acad. Sci. USA), vol. 99, No. 4, pp. 2140-2145, 2002). For example, when retrovirus or lentivirus is used, cells are sown to an appropriate incubator such as a culture dish, a virus vector is added to the culture broth (if desired, polybrene may be co-present), the cells are cultured for 1 to 2 days, after which, cultivation is continued as described above, and cells having the vector integrated therein are selected.

A prothymosin α gene-modified non-human mammal having a prothymosin α gene sandwiched between loxP sequences can be generated by the above-mentioned method. In addition, a currently existing prothymosin α gene-modified non-human mammal may be obtained and used.

A non-human mammal wherein prothymosin α gene in the striatum is knocked out can be obtained by crossing a prothymosin α gene-modified non-human mammal having the prothymosin α gene sandwiched between the aforementioned loxP sequences and a genetically-modified non-human mammal having a striatum—specifically expressed cre gene.

As a specific means for introducing a striatum—specifically expressed cre gene, a method including introducing a DNA encoding a Cre protein by techniques for preparation of transgenic animals known per se, and allowing striatum-specific expression in the subject non-human mammal and the like can be mentioned.

A DNA encoding a Cre protein may be a DNA encoding a Cre protein derived from bacteriophage P1 or a protein having an amino acid sequence substantially the same therewith. As the DNA encoding a Cre protein, a DNA encoding the amino acid sequence registered in the GenBank as accession No. YP_006472.1 can be mentioned. As the "substantially the same amino acid sequence", an amino acid sequence having about 90% or more, preferably about 95% or more, more preferably about 98% or more identity with the aforementioned amino acid sequence and the like can be mentioned. The identity of the amino acid sequence can be calculated using the homology calculation algorithm NCBI BLAST (National Center for Biotechnology Information Basic Local Alignment Search Tool) under the following conditions (expect=10; gap allowed; matrix=BLOSUM62; filtering=OFF).

As a protein having substantially the same amino acid sequence, a protein containing the aforementioned amino acid sequence and having substantially the same activity as that of a protein consisting of the amino acid sequence is preferable. As the substantially the same activity, loxP sequence binding action, cleaving out action on a DNA sequence flanked with loxP and the like can be mentioned. Substantially the same means that these activities are qualitatively equivalent. Therefore, activities such as loxP sequence binding action, cleaving out action on a DNA sequence flanked with loxP and the like are preferably equivalent. However, quantitative factors such as the degrees of these activities (e.g., about 0.01 to 100 times, preferably about 0.5 to 20 times, more preferably about 0.5 to times) and the molecular weight of the protein may be different. As the DNA encoding a Cre protein, a DNA contained in the base sequence registered as GenBank accession No. NC_005856.1 can be used.

The DNA encoding a Cre protein can be isolated by a hybridization method or PCR method using a cDNA prepared by a known method and using all or a part of a DNA or RNA derived from bacteriophage P1 as a starting material, and an oligonucleotide prepared on the basis of a commonly known cre gene sequence as the probe or primer, and the like.

The genetically-modified non-human mammal having a striatum—specifically expressed cre gene of the present invention maintains a DNA encoding the Cre protein in a "state specifically expressible in the striatum". Therefore, to introduce the DNA into a subject animal, the DNA needs to be used in a form containing an expression cassette wherein the DNA is joined downstream of a promoter capable of functioning only in the striatum of the subject animal (e.g., expression vector and the like).

Examples of the vector carrying a DNA encoding the Cre protein include plasmids amplified with *Escherichia coli*, *Bacillus subtilis*, or yeast, bacteriophages such as λ phage, retroviruses such as Moloney leukemia virus, animal or insect viruses such as lentivirus, adeno-associated virus, vaccinia virus and baculovirus, and the like. In particular, plasmids (preferably plasmids from *Escherichia coli*, *Bacillus subtilis*, or yeast, particularly plasmids from *Escherichia coli*) and animal viruses (preferably retrovirus, lentivirus) are preferable.

A promoter used to control gene expression of the Cre protein needs to be a promoter capable of functioning in the striatum of a target non-human mammal. Examples of such promoter include G protein γ7 subunit gene (Gng7) promoter, Distal-less homeobox protein 5/6(Dlx5/6) promoter, Tyrosine Hydroxylase promoter and the like. Of these, as a promoter showing a striatum-specific high expression, G protein γ7 subunit gene (Gng7) promoter is particularly preferably used.

It is preferable that a sequence that terminates the transcription of the desired messenger RNA in the non-human mammal (a polyadenylation (polyA) signal, also called a terminator) be present downstream of the DNA that encodes a Cre protein; for example, using a terminator sequence derived from a virus gene, or derived from a gene of various mammals or birds, efficient expression of the transgene can be achieved. Preferably, the SV40 terminator of simian virus and the like are used. In addition, for the purpose of increasing the expression of the desired gene, the splicing signal of each gene, an enhancer region, or a portion of the intron of an eukaryotic gene can also be joined 5' upstream of the promoter region, between the promoter region and the coding region, or 3' downstream of the coding region, depending on the purpose.

When a non-human mammal is prepared using an embryonic stem cell (ES cell), the above-described vector preferably further comprises a selection marker gene (e.g., drug resistance genes such as neomycin resistance gene and hygromycin resistance gene) for selecting a clone having the introduced DNA stably integrated therein. Furthermore, when it is intended to integrate the introduced DNA at a particular location on the host chromosome by homologous recombination (i.e., preparation of a knockin animal), the above-described vector preferably further comprises the herpes simplex virus-derived thymidine kinase (HSV-tk) gene or the diphtheria toxin gene as a negative selection marker gene outside a DNA sequence homologous to the target site, in order to avoid random insertions.

The above-described promoter, DNA that encodes a Cre protein, terminator and the like can be inserted into the above-described vector in the right arrangement, i.e., in an arrangement that allows the expression of the Cre protein in the non-human mammal, by an ordinary gene engineering technique using an appropriate restriction enzyme and DNA ligase and the like.

For introducing an expression vector comprising a DNA that encodes Cre protein into a cell, a method known per se is used as appropriate according to the target cell. For example, for introduction into an early embryo such as a fertilized egg, the microinjection method is used. For introduction into an ES cell, the calcium phosphate co-precipitation method, electroporation method, lipofection method, retrovirus infection method, aggregation method, microinjection method, particle gun method, DEAE-dextran method and the like can be used. Alternatively, when retrovirus, lentivirus and the like are used as the vector, it is sometimes possible to achieve gene introduction conveniently by adding the virus to an early embryo or an ES cell, and culturing the embryo or cell for 1 to days to infect the cells with the virus. Regeneration of individuals from an ES cell (establishment of founder), passage (preparation of homozygotes) and the like can be performed as described above with respect to the prothymosin α gene-modified non-human mammal of the present invention.

In a preferred embodiment, the expression vector comprising a DNA that encodes Cre protein is introduced into an early embryo of a non-human mammal being the subject by microinjection.

An early embryo of the subject non-human mammal can be obtained by collecting an in vivo fertilized egg obtained by mating a male and female non-human mammal of the same species, or by in vitro fertilization of an ovum and spermatozoa collected from a female and male non-human mammal of the same species, respectively.

The age, rearing conditions and the like of the non-human mammal used vary depending on animal species; for example, when a mouse (preferably, a mouse of an inbred strain such as C57BL/6J(B6), $F_1$ of B6 and another inbred strain, and the like) is used, it is preferable that a female at about 4 to about 6 weeks of age and a male at about 2 to about 8 months of age be used, and that the mice be used after rearing with a bright phase of about 12 hours (for example, 7:00-19:00) for about 1 week.

Although the in vivo fertilization may be by spontaneous mating, a method is preferable comprising administering a gonadotropic hormone to a female non-human mammal to induce overovulation, and then mating the female with a male non-human mammal, for the purpose of adjusting the estrous cycle and obtaining a large number of early embryos from a single individual. For inducing ovulation in a female non-human mammal, for example, a method is preferable comprising administering a follicle-stimulating hormone (pregnant mare's serum gonadotropic hormone, generally abbreviated as PMSG), and then a luteinizing hormone (human chorionic gonadotropic hormone, generally abbreviated as hCG), by, for example, intraperitoneal injection and the like; preferable amounts and frequencies of administration of the hormones vary depending on the species of the non-human mammal. For example, when the non-human mammal is a mouse (preferably, a mouse of an inbred strain such as C57BL/6J(B6), $F_1$ of B6 and another inbred strain, and the like), a method is preferable comprising administering a follicle-stimulating hormone, then administering a luteinizing hormone about 48 hours later, and immediately mating the female mouse with a male mouse to obtain a fertilized egg, wherein the amount of the follicle-stimulating hormone administered is about 20 to about 50 IU/individual, preferably about 30 IU/individual, and the amount of the luteinizing hormone administered is about 0 to about 10 IU/individual, preferably about 5 IU/individual.

After elapse of a given time, a female non-human mammal confirmed to have copulated by vaginal plug examination and the like is laparotomized, a fertilized egg is removed from the oviduct, washed in a medium for embryo culture (e.g., M16 medium, modified Whitten medium, BWW medium, M2 medium, WM-HEPES medium, BWW-HEPES medium and the like) to remove cumulus oophorus cells, and cultured in 5% gaseous carbon dioxide/95% atmosphere by the microdrop culture method and the like until DNA microinjection. If microinjection is not immediately performed, the fertilized egg collected may be stored under freezing by the slow method or the ultrarapid method and the like.

Meanwhile, in the case of in vitro fertilization, a follicle-stimulating hormone and a luteinizing hormone are administered to a female non-human mammal for egg collection (the same as with in vivo fertilization is preferably used) as described above to induce ovulation, after which ova are collected and cultured in a medium for fertilization (e.g., TYH medium) in 5% gaseous carbon dioxide/95% atmosphere by the microdrop culture method and the like until in vitro fertilization. Separately, the cauda epididymidis is removed from a male non-human mammal of the same species (the same as with in vivo fertilization is preferably used), and a spermatozoa mass is collected and precultured in a medium for fertilization. After completion of the preculture, spermatozoa are added to the medium for fertilization containing the ova, and the ova are cultured in 5% gaseous carbon dioxide/95% atmosphere by the microdrop culture method and the like, after which a fertilized egg having two pronuclei is selected under a microscope. If DNA microinjection is not immediately performed, the fertilized egg obtained may be stored under freezing by the slow method or the ultrarapid method and the like.

DNA microinjection into the fertilized egg can be performed by a conventional method using a commonly known device such as a micromanipulator. Briefly, the fertilized egg placed in a microdrop of a medium for embryo culture is aspirated and immobilized using a holding pipette, and a DNA solution is injected directly into the male or female pronucleus, preferably into the male pronucleus, using an injection pipette. The introduced DNA is used preferably after being highly purified using CsCl density gradient ultracentrifugation or an anion exchange resin column and the like. It is also preferable that the introduced DNA be linearized in advance by cutting the vector portion using a restriction endonuclease.

After introducing the DNA, the fertilized egg is cultured in a medium for embryo culture in 5% gaseous carbon dioxide/95% atmosphere by the microdrop culture method and the like until the 1-cell stage to blastocyst stage, after which it is transplanted to the oviduct or uterus of a female non-human mammal for embryo reception rendered to be pseudopregnant. The female non-human mammal for embryo reception may be any one of the same species as the animal from which the early embryo to be transplanted is derived; for example, when a mouse early embryo is transplanted, a female ICR mouse (preferably about 8 to about 10 weeks of age) and the like are preferably used. A known method of rendering a female non-human mammal for embryo reception pseudopregnant is, for example, a method comprising mating the female with a vasectomized (vasoligated) male non-human mammal of the same species (for example, in the case of a mouse, with a male ICR mouse (preferably about 2 months or more of age)), and selecting a female confirmed to have a vaginal plug.

The female for embryo reception used may be one that has ovulated spontaneously, or one receiving luteinizing hormone releasing hormone (generally abbreviated as LHRH) or an analogue thereof administered prior to mating with a vasectomized (vasoligated) male, to induce fertility. Examples of the LHRH analogue include [3,5-DiI-Tyr$^5$]-LH-RH, [Gln$^8$]-LH-RH, [D-Ala$^6$]-LH-RH, [des-Gly$^{10}$]-LH-RH, [D-His(Bzl)$^6$]-LH-RH and Ethylamides thereof and the like. The amount of LHRH or an analogue thereof administered, and the time of mating with a male non-human mammal after the administration vary depending on the species of the non-human mammal. For example, when the non-human mammal is a mouse (preferably an ICR mouse and the like), it is usually preferable that the female mouse be mated with a male mouse about 4 days after administration of LHRH or an analogue thereof; the amount of LHRH or an analogue thereof administered is usually about 10 to 60 μg/individual, preferably about 40 μg/individual.

Usually, if the early embryo to be transplanted is in the morula stage or after, the embryo is transplanted to the uterus of a female for embryo reception; if the early embryo is in a stage before the morula stage (for example, 1-cell stage to 8-cell stage embryo), the embryo is transplanted to the oviduct. The female for embryo reception is used as appropriate after elapse of a given number of days after becoming pseudopregnant depending on the developmental stage of the embryo to be transplanted. For example, in the case of a mouse, a female mouse at about 0.5 days after becoming pseudopregnant is preferable for the transplantation of a 2-cell stage embryo, and a female mouse at about 2.5 days after becoming pseudopregnant is preferable for the transplantation of a blastocystic embryo. After the female for embryo reception is anesthetized (preferably, Avertin, Nembutal and the like are used), an incision is made, the ovary is pulled out, and early embryos (about 5 to about 10 embryos) in suspension in a medium for embryo culture are injected into the vicinity of the abdominal osteum of the uterine tube or the uterine tube junction of the uterine horn using a pipette for embryo transplantation.

If the transplanted embryo implants successfully and the embryo recipient female becomes pregnant, non-human mammal pups will be obtained by spontaneous delivery or caesarian section. Embryo recipient females that have delivered spontaneously are allowed to continue suckling; if the pups are delivered by caesarian section, the pups can be suckled by a separately provided female for suckling (for example, in the case of the mouse, a female mouse with usual mating and delivery (preferably a female ICR mouse and the like)).

Transfer of the DNA that encodes Cre protein in the fertilized egg cell stage is secured so that the introduced DNA will be present in all of the germline cells and somatic cells of the subject non-human mammal. Whether or not the introduced DNA is integrated in chromosome DNA can be determined by, for example, screening chromosome DNAs separated and extracted from the tail of the pup, by Southern hybridization or PCR. The presence of the Cre protein encoding DNA in the germline cells of the offspring non-human mammal ($F_0$) obtained as described above means that the Cre protein encoding DNA is present in all of the germline cells and somatic cells of all animals in the subsequent generation ($F_1$).

Usually, $F_0$ animals are obtained as heterozygotes having the introduced DNA in either of the homologous chromosomes. Different $F_0$ individuals have the introduced DNA inserted randomly on different chromosomes unless the insertion is by homologous recombination. To obtain a homozygote having the introduction DNA in both of the homologous chromosomes, an $F_0$ animal and a non-transgenic animal are crossed to prepare an $F_1$ animal, and heterozygous siblings thereof having the introduced DNA in either of the homologous chromosomes may be crossed. If the introduced DNA is integrated only at one gene locus, ¼ of the $F_2$ animals obtained will be homozygotes.

In another preferred embodiment with the use of a virus as the vector, as with the above-described case of prothymosin α gene-modified non-human mammal, a method comprising infecting an early embryo or ES cell of a non-human mammal with a virus comprising a DNA that encodes Cre protein can be mentioned. When a fertilized egg is used as the cell, it is preferable that the zone pallucida be removed prior to infection. After cultivation for 1 to 2 days following infection with the virus vector, the fertilized egg is transplanted to the oviduct or uterus of a female non-human mammal for embryo reception rendered to be pseudopregnant as described above in the case of an early embryo, or the fertilized egg is continued to be cultured with the addition of a selection drug as described above in the case of an ES cell, and a cell incorporating the vector is selected.

Furthermore, as described in the Proceedings of the National Academy of Sciences, USA (Proc. Natl. Acad. Sci. USA), vol. 98, pp. 13090-13095, 2001, a spermatogonium collected from a male non-human mammal is infected with a virus vector during co-cultivation with STO feeder cells, after which the spermatogonium is injected into the seminiferous tube of a male infertile non-human mammal, and the male infertile non-human mammal is mated with a female non-human mammal, whereby pups that are hetero non-human mammal (+/−) for a DNA that encodes Cre protein can be obtained efficiently.

A genetically-modified non-human mammal having a striatum—specifically expressed Cre gene can be generated by the above-mentioned method; however, a currently existing prothymosin α gene-modified non-human mammal may be obtained and used.

When a genetically-modified non-human mammal having a striatum—specifically expressed Cre gene is crossed with the aforementioned prothymosin α gene-modified non-human mammal having a prothymosin α gene sandwiched between loxP sequences, homozygotes are desirably crossed. For example, $F_1$ obtained by crossing Gng7-Cre(+/+) mouse as a genetically-modified non-human mammal having a striatum—specifically expressed cre gene, and ProTa flox(+/+) mouse as prothymosin α gene-modified non-human mammal having a prothymosin α gene flanked with loxP sequences is Gng7-Cre(+/−)×ProTa flox(+/−) in all individuals. By crossing the $F_1$ individuals, Gng7-Cre(+/−)×ProTa flox(+/+) is obtained with 1/8 probability. Therefore, by crossing the obtained male Gng7-Cre(+/−)×ProTa flox(+/+) mouse and a female ProTa flox(+/+) mouse, Gng7-Cre(+/−)×ProTa flox(+/+) can be efficiently obtained with a high probability of 1/2. In consideration of the influence of the effect of homozygous knockout of the prothymosin α gene in the above-mentioned crossing method on the matrix, it is most preferable to cross a male (Gng7-Cre(+/−)×ProTa flox(+/+)) and a female (ProTa flox(+/+)). The prothymosin α gene is preferably homozygous knockout in the striatum. Therefore, as a non-human mammal wherein prothymosin α gene is knocked out in the striatum, a non-human mammal having a cre gene showing an expression controlled by a G protein γ7 subunit gene promoter, and having a homozygous prothymosin α gene flanked with loxP sequences can be preferably mentioned.

The non-human mammal deficient in the expression of prothymosin α gene in the striatum also includes a conditional knocked-down (KD) non-human mammal wherein expression of prothymosin α gene is inactivated in the striatum by antisense or RNAi technique.

Regarding specific means for knocking down prothymosin α gene in the striatum, a method comprising introducing a DNA that encodes an antisense RNA or siRNA (including siRNA) of prothymosin α using techniques of preparation of transgenic animals known per se, and striatum—specifically allowing it to express in the subject non-human mammal and the like can be mentioned.

A DNA comprising a base sequence complementary to the target region of a desired polynucleotide, i.e., a DNA hybridizable with a desired polynucleotide, can be said to be "antisense" against the desired polynucleotide.

The antisense DNA having a base sequence complementary or substantially complementary to the base sequence of a polynucleotide that encodes prothymosin α or a portion thereof may be any antisense DNA, as long as it contains a base sequence complementary or substantially complementary to the base sequence of the polynucleotide that encodes prothymosin α or a portion thereof, and having an action to suppress the expression of the polynucleotide.

The base sequence substantially complementary to a polynucleotide that encodes prothymosin α is, for example, a base sequence having a homology of about 70% or more, preferably about 80% or more, more preferably about 90% or more, most preferably about 95% or more, to the base sequence of the complementary strand of the polynucleotide for the overlapping region. Base sequence homology herein can, for example, be calculated using the homology calculation algorithm NCBI BLAST (National Center for Biotechnology Information Basic Local Alignment Search Tool) under the following conditions (expect=10; gap allowed; filtering=ON; match score=1; mismatch score=−3).

Particularly, of the full base sequence of the complementary strand of the polynucleotide that encodes prothymosin α, (a) in the case of an antisense DNA intended to inhibit the translation, an antisense DNA having a homology of about 70% or more, preferably about 80% or more, more preferably about 90% or more, most preferably about 95% or more, to the complementary strand of the base sequence of the portion that encodes the N-terminal part of prothymosin α protein (e.g., a base sequence in the vicinity of the initiation codon and the like) is suitable, and (b) in the case of an antisense DNA intended to degrade RNA with RNaseH, an antisense DNA having a homology of about 70% or more, preferably about 80% or more, more preferably about 90% or more, most preferably about 95% or more, to the complementary strand of the full base sequence of the polynucleotide that encodes prothymosin α including the intron, is suitable.

Specifically, when the subject non-human mammal is a mouse, an antisense DNA comprising a base sequence complementary or substantially complementary to the base sequence registered under GenBank accession No. NM_008972.2 or a portion thereof, preferably, an antisense DNA comprising a base sequence complementary to the base sequence or a portion thereof, and the like can be mentioned. When the subject non-human mammal is a rat, an antisense DNA comprising a base sequence complementary or substantially complementary to the base sequence registered under GenBank accession No. NM_021740.1 or a portion thereof, preferably, an antisense DNA comprising a base sequence complementary to the base sequence or a portion thereof, and the like can be mentioned.

An antisense DNA having a base sequence complementary or substantially complementary to the base sequence of a polynucleotide that encodes prothymosin α or a portion thereof (hereinafter, also referred to as "the antisense DNA of the present invention") can be designed and synthesized on the basis of base sequence information on a DNA that encodes cloned or determined prothymosin α. Such antisense DNA is capable of inhibiting the replication or expression of the prothymosin α gene. Specifically, the antisense DNA of the present invention is capable of hybridizing with an RNA transcribed from the prothymosin α gene (mRNA or initial transcription product), and capable of inhibiting the synthesis (processing) or function (translation into protein) of mRNA.

The target region of the antisense DNA of the present invention is not particularly limited with respect to the length thereof, as long as the translation into prothymosin α protein is inhibited as a result of hybridization of the antisense DNA; the target region may be the entire sequence or a partial sequence of the mRNA that encodes the protein, and the length is about 10 bases for the shortest, and the entire sequence of the mRNA or initial transcription product for the longest. Specifically, the 5' end hairpin loop, 5' end 6-base-pair repeats, 5' end untranslated region, translation initiation codon, protein coding region, ORF translation stop codon, 3' end untranslated region, 3' end palindrome region, or 3' end hairpin loop of the prothymosin α gene may be chosen as a preferable target region of the antisense DNA, but any other region in the prothymosin α gene may also be chosen as the target. For example, the intron portion of the gene may also be the target region.

Furthermore, the antisense DNA of the present invention may be one that not only hybridizes with the mRNA or initial transcription product of prothymosin α to inhibit the translation into protein, but also is capable of binding to the prothymosin α gene being a double-stranded DNA to form a triple strand (triplex) and hence to inhibit the transcription to RNA. Alternatively, the antisense DNA of the present invention may be one that forms a DNA:RNA hybrid to induce the degradation by RNaseH.

A DNA that encodes a ribozyme capable of specifically cleaving the mRNA that encodes prothymosin α or the initial transcription product within the coding region (including the intron portion in the case of the initial transcription product) can also be encompassed in the antisense DNA of the present invention. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends flanking to the hammerhead structure portion (about 10 bases in total) a sequence complementary to the desired cleavage site of the mRNA. Because this type of ribozyme has only RNA as the substrate, it offers an additional advantage of non-attack of genomic DNA. Provided that the prothymosin α mRNA assumes a double-stranded structure per se, the target sequence can be made to be single-stranded by using a hybrid ribozyme prepared by joining an RNA motif derived from a viral nucleic acid that can bind specifically to RNA helicase [Proc. Natl. Acad. Sci. USA, 98(10): 5572-5577 (2001)]. Furthermore, the ribozyme may be a hybrid ribozyme prepared by further joining a sequence modified from the tRNA to promote the translocation of the transcription product to cytoplasm [Nucleic Acids Res., 29(13): 2780-2788 (2001)].

Herein, a double-stranded DNA consisting of an oligo-RNA homologous to a partial sequence (including the intron portion in the case of the initial transcription product) in the coding region of the mRNA or initial transcription product of prothymosin α and a strand complementary thereto, what is called a short-chain interfering RNA (siRNA), can also be used to prepare the KD animal of the present invention. It had been known that so-called RNA interference (RNAi), which is a phenomenon that when siRNA is introduced into cells, an mRNA homologous to the RNA is degraded, occurs in nematodes, insects, plants and the like; since this phenomenon was confirmed to also occur in animal cells [Nature, 411(6836): 494-498 (2001)], siRNA has been widely utilized as an alternative technique to ribozymes. siRNA can be designed as appropriate on the basis of base sequence information of the mRNA being the target using commercially available software (e.g., RNAi Designer; Invitrogen).

The antisense oligo-DNA and ribozyme of the present invention can be prepared by determining the target sequence for the mRNA or initial transcription product on the basis of a cDNA sequence or genomic DNA sequence of prothymosin α, and synthesizing a sequence complementary thereto using a commercially available DNA/RNA synthesizer (Applied Biosystems, Beckman, and the like). By inserting the synthesized antisense oligo-DNA or ribozyme downstream of the promoter in the expression vector, via an appropriate linker (adapter) sequence used as required, a DNA expression vector that encodes the antisense oligo-RNA or ribozyme can be prepared. Examples of expression vectors that can be used preferably here include plasmids amplified with *Escherichia coli, Bacillus subtilis*, or yeast, bacteriophages such as λ phage, retroviruses such as Moloney leukemia virus, animal or insect viruses such as lentivirus, adeno-associated virus, vaccinia virus and baculovirus, and the like. In particular, plasmids (preferably plasmids from *Escherichia coli, Bacillus subtilis*, or yeast, particularly plasmids from *Escherichia coli*) and animal viruses (preferably retrovirus, lentivirus) are preferable.

In addition, a promoter for expressing an antisense oligoDNA in the present invention needs to show a striatum-specific expression. Examples of such promoter include a G protein γ7 subunit gene (Gng7) promoter.

A DNA expression vector that encodes a longer antisense RNA (e.g., full-length complementary strand of prothymosin α mRNA and the like) can be prepared by inserting a prothymosin α cDNA, cloned by a conventional method, in the reverse direction, via an appropriate linker (adapter) sequence used as required, downstream of the promoter in the expression vector.

Meanwhile, a DNA that encodes siRNA can be prepared by separately synthesizing a DNA that encodes a sense strand and a DNA that encodes an antisense strand, and inserting them into an appropriate expression vector. In this case, in the animal cell incorporating the vector, the sense strand and the antisense strand are transcribed and annealed to form siRNA. shRNA can be prepared by inserting a unit comprising a sense strand and an antisense strand separated by a length base allowing the formation of an appropriate loop structure (e.g., about 15 to 25 bases) into an appropriate expression vector. In this case, the shRNA transcribed in the animal cell incorporating the expression vector forms a loop by itself, and is then processed by an endogenous enzyme dicer and the like to form mature siRNA. A promoter in a vector expressing siRNA or shRNA needs to show a striatum—specifically expression. Examples of such promoter include a G protein γ7 subunit gene (Gng7) promoter.

A method for introducing an expression vector comprising a DNA that encodes an antisense RNA, siRNA, shRNA, or miRNA of prothymosin α into a cell, an early embryo such as a fertilized egg introduced with the DNA, regeneration of individuals from an ES cell (establishment of founder), passage (preparation of homozygotes) and the like can be similar to those in the method of generating a genetically-modified non-human mammal having a striatum—specifically expressed Cre gene using the aforementioned DNA encoding the Cre protein.

The non-human mammal deficient in the expression of prothymosin α gene in the striatum in the present invention shows the following properties as compared to the corresponding wild-type animal:
(1) vulnerable to cerebral ischemia produced by a treatment,
(2) inferior in motility,
(3) spontaneously developing the condition of the above-mentioned (1) and/or (2) by aging, and
(4) showing improve symptoms of the above-mentioned (1), (2) or (3) by a dopamine D2 receptor agonist, a dopamine metabolism inhibitor, an NMDA receptor antagonist or a dopamine D1 receptor agonist. These phenotypes partly match with the phenotypes of huntingtin transgenic mouse and huntingtin knock-in mouse as conventionally-known Huntington's disease model mice. However, since the nerve cells of the whole striatum are injured in these mice, the above-mentioned phenotypes show fast progression and are more serious, and therefore, do not accurately reflect the actual pathology of Huntington's disease. Moreover, since the non-human mammal deficient in the expression of prothymosin α gene in the striatum in the present invention shows abnormal motility, it matches with the phenotype of a model mouse showing dystonia symptoms. Here, dystonia may be developed from an ischemic disease (secondary dystonia), and ischemic disease includes, for example, cerebral infarction (cerebral thrombus, cerebral embolism).

Being vulnerable to a cerebral ischemia produced by a treatment means that the survival ratio decreases as compared to the corresponding wild-type animal by, for example, ligating the middle cerebral artery of the non-human mammal of the present invention. Being inferior in the motility means that, irrespective of the presence or absence of ligation of the middle cerebral artery, the motility function and motor coordination are inferior as compared to the corresponding wild-type animal. In addition, the non-human mammal of the present invention spontaneously develops, due to aging, vulnerability to cerebral ischemia produced by a treatment and inferior motility symptom. For example, a Gng cre/+; ProTa flox/flox mouse shows the above-mentioned symptoms at the age of about 10 weeks as compared to the corresponding wild-type mouse, which become aggravated as the weeks of age increase and, remarkable difference in the symptom can be confirmed at about 20 weeks of age as compared to the wild-type mouse. These symptoms are suggested to be caused by the deletion of the functional prothymosin α from the striatum GABA neuron that expresses excitatory dopamine D1 receptor and the loss of a neuroprotecting action. Moreover, the non-human mammal of the present invention shows improvement in the aforementioned symptoms upon administration of a dopamine D2 receptor agonist expected to show a supplementation effect of the action of excitatory dopamine D1 receptor, a dopamine metabolism inhibitor, an NMDA receptor antagonist expected to show an effect of protecting nerve cells from glutamic acid or a dopamine D1 receptor agonist expected to show a supplementation effect of the action of suppressive dopamine D2 receptor. Here, as the dopamine D2 receptor agonist, pramipexole, pergolide, cabergoline, talipexole, ropinirole and the like can be mentioned. As the dopamine metabolism inhibitor, selegiline, entacapone, amantadine having a dopamine liberation action, L-DOPA which is a dopamine precursor, L-DOPA as a pro-drug, droxidopa, zonisamide involved in the increased expression of dopamine synthase and the like, and the like can also be mentioned. As the NMDA receptor antagonist, memantine, CP-101606 (IUPAC name: (1S,2S)-1-(4-hydroxyphenyl)-2-(4-hydroxy-4-phenylpiperidino)-1-propanol) and the like can be mentioned. As the dopamine D1 receptor agonist, SKF38393 (SKF38393 HCl, (±)-1-phenyl-2,3,4,5-tetrahydro-1H-3-benzazepine-7,8-diol HCl), SKF81297 (6Chloro1phenyl2,3,4,5tetrahydro1H3benzazepine7,8diol), Doxanthrine and the like can be mentioned.

Based on these findings, it is strongly suggested that the deficient expression of prothymosin α gene in the striatum is involved in not only the onset and progression of neurodegenerative diseases through a decrease in the striate nuclei nerval function, but also deeply involved in the onset and progression of dystonia. Therefore, the non-human mammal of the present invention provides a screening method for a therapeutic/prophylactic drug for a neurodegenerative disease or dystonia due to an ischemic disease, comprising applying a test substance and measuring (1) a survival ratio in a cerebral ischemia produced by a treatment and/or (2) motility. Furthermore, as mentioned above, the non-human mammal of the present invention spontaneously develops, with aging, vulnerability to cerebral ischemia produced by a treatment and inferior motility symptoms, and particularly, the survival ratio may decrease even in the absence of cerebral ischemia produced by a treatment. Accordingly, the non-human mammal of the present invention with age also provides a screening method for a therapeutic/prophylactic drug for a neurodegenerative disease or dystonia due to an ischemic disease, comprising applying a test substance and measuring (1) a survival ratio and/or (2) motility. The age in weeks is about 10-week-old or above, preferably about 20-week-old or above.

Specifically, in the screening method, a test substance is administered to the non-human mammal of the present invention. Useful test substances include, in addition to commonly known synthetic compounds, peptides, proteins, DNA libraries and the like, for example, tissue extracts, cell culture supernatants and the like of mammals (for example, mice, rats, pigs, bovines, sheep, monkeys, humans and the like). Preferably, dopamine D2 receptor agonist, dopamine metabolism inhibitor, NMDA receptor antagonist or dopamine D1 receptor agonist can be used. As the dopamine D2 receptor agonist, dopamine metabolism inhibitor, NMDA receptor antagonist and dopamine D1 receptor agonist, those exemplified above can be mentioned. A survival ratio controlling action and/or a motility regulating action of a test substance on cerebral ischemia produced by a treatment can be each measured by methods known per se, for example, the methods used in an Example below and the like. In addition, as a result of the measurement, a test substance that improves a survival ratio in cerebral ischemia produced by a treatment and/or motility as compared to the non-human mammal of the present invention free of administration of the test substance is preferably selected.

As a disease that can be prevented or treated by a test substance having a controlling action on the survival ratio in cerebral ischemia produced by a treatment and/or a motility regulating action, which is selected by the screening method, neurodegenerative diseases (e.g., Huntington's disease, Alzheimer, Parkinson's disease, neurosis (e.g., melancholia, anxiety etc.), dystonia, progressive supranuclear palsy, amyotrophic lateral sclerosis, striato-nigral degeneration, Shy-Drager syndrome, olivopontocerebellar atrophy and the like can be mentioned. Furthermore, the test substance can also is prevent or treat dystonia derived from ischemic disease, in an attempt to improve motility disorders.

A therapeutic/prophylactic drug for neurodegenerative diseases and the like can, for example, be used orally as tablets coated with sugar as required, capsules, elixirs, microcapsules and the like, or can be used parenterally in the form of an injection such as a sterile solution or suspension in water or another pharmaceutically acceptable liquid. The therapeutic/prophylactic drug can be prepared as pharmaceutical preparations by being blended with a physiologically acceptable carrier, flavoring agent, filler, vehicle, antiseptic, stabilizer, binder and the like, in a unit dosage form required for generally accepted preparation design. The amounts of active ingredients in these preparations are chosen as appropriate in consideration of the doses described below.

Examples of additives that can be blended in tablets, capsules and the like include binders like gelatin, cornstarch, tragacanth and acacia, fillers like crystalline cellulose, swelling agents like cornstarch, gelatin, alginic acid and the like, lubricants like magnesium stearate, sweeteners like sucrose, lactose or saccharin, flavoring agents like peppermint, acamono oil or cherry, and the like. When the formulation unit form is a capsule, the above-described type of material can further contain a liquid carrier like an oil or fat. A sterile composition for injection can be formulated according to an ordinary procedure for pharmaceutical making, such as dissolving or suspending an active substance in a vehicle like water for injection, or a naturally occurring vegetable oil such as sesame oil or coconut oil.

The aqueous solution for injection is exemplified by saline, isotonic solutions containing glucose and another auxiliary (e.g., D-sorbitol, D-mannitol, sodium chloride and the like) and the like, and may be used in combination with an appropriate solubilizer, for example, an alcohol (e.g., ethanol), a polyalcohol (e.g., propylene glycol, polyethylene glycol and the like), a non-ionic surfactant (e.g., Polysorbate 80™, HCO-50 and the like) and the like. The oily liquid is exemplified by sesame oil, soybean oil and the like, and may be used in combination with a solubilizer such as benzyl benzoate or benzyl alcohol. Also, the aqueous solution for injection may be formulated with, for example, a buffering agent (e.g., phosphate buffer solution, sodium acetate buffer solution and the like), a soothing agent (e.g., benzalkonium chloride, procaine hydrochloride and the like), a stabilizer (e.g., human serum albumin, polyethylene glycol and the like), a preservative (e.g., benzyl alcohol, phenol and the like), an antioxidant and the like. The injectable preparation prepared is usually filled in an appropriate ampoule.

Since the preparation thus obtained is safe and of low toxicity, it can be administered to, for example, mammals (e.g., humans, rats, mice, guinea pigs, rabbits, sheep, pigs, bovines, horses, cats, dogs, monkeys and the like).

The dose of the therapeutic/prophylactic drug for neurodegenerative diseases and the like varies depending on the target disease, subject of administration, route of administration and the like; for example, in the case of oral administration for treatment of neurodegenerative disease, the usual dosage for an adult (weighing 60 kg) is about 0.1 mg to about 100 mg, preferably about 1.0 to about 50 mg, more preferably about 1.0 to about 20 mg, per day. In the case of parenteral administration, the dose of the therapeutic/prophylactic drug varies depending on the subject of administration, target disease and the like; for example, in the case of administration as an injection to an adult (weighing 60 kg) for treatment of neurodegenerative disease, the dose is about 0.01 to about 30 mg, preferably about 0.1 to about 20 mg, more preferably about 0.1 to about 10 mg, per day. When the subject of administration is a non-human animal, an amount converted per 60 kg of body weight can be administered.

EXAMPLES

The present invention is explained in more detail in the following by referring to Examples and Reference Examples, which are not to be construed as limitative.

Example 1

Production of Gene Recombinant Mouse

In addition to male C57BL/6J mouse (wild-type mouse), male TG mouse (Gng7-Cre(+/−) mouse) expressing homologous recombinase (Cre) controlled by a promoter of Gng7 specifically expressing in the striatum, and further, conditional gene deficient mouse (Gng cre/+; ProTa flox/flox male mouse) obtained by crossing Gng7-Cre(+/−) and Floxed prothymosin α gene recombinant mouse were used for the experiment. As the both mice, 8- to 16-week-old younger mice and 20- to 30-week-old older mice, both having a body weight of 20-35 g, were used. The breeding conditions were: constant temperature (22±2° C.), constant humidity (55±5%), a solid feed for general experiment (MF, Oriental Yeast Co., ltd., Tokyo) and free ingestion of tap water. All experiments were performed according to the method determined in the animal experiment regulations of Nagasaki University. The male Gng7-Cre(+/+) mice were provided by Dr. Masayoshi Mishina, Molecular Neurobiology, Faculty of Medicine, graduate school, the University of Tokyo, and the Floxed prothymosin α gene recombinant mice were provided by Otsuka Pharmaceutical Co., Ltd.

The structure of wild-type allele of the mouse prothymosin α gene is as shown in the upper panel of FIG. 1. In Floxed allele, which is contained in Floxed prothymosin α gene recombinant mouse, loxP sequence is inserted between exons and 2, and exons 3 and 4 such that it is in tandem with each of them (FIG. 1, middle panel), and Cre protein acts on the loxP sequence, whereby a sequence containing exons 2 and 3, which are sandwiched between two loxP sequences is deleted (FIG. 1, the lower panel). The Cre protein is connected to the downstream of Gng7 promoter, which is a striatum-specific expression promoter, and the above-mentioned conditional mouse shows striatum-specific functional deficiency of the prothymosin α gene. In this Example, unless particularly indicated separately, WT is a wild-type mouse (C57BL/J6), Gg is a Gng7-Cre(+/−) mouse, that is, a mouse inserted with a cre gene at the downstream of Gng7 promoter to form a heterozygote, and GgFF is a mouse wherein prothymosin α is deleted by the cre-loxP system specifically to the striatum region of the basal nucleus which is a Gng7 expression region.

Example 2

Pathology of Young Mouse Deficient in Prothymosin in Striatum Due to Ischemia

Figure 2:
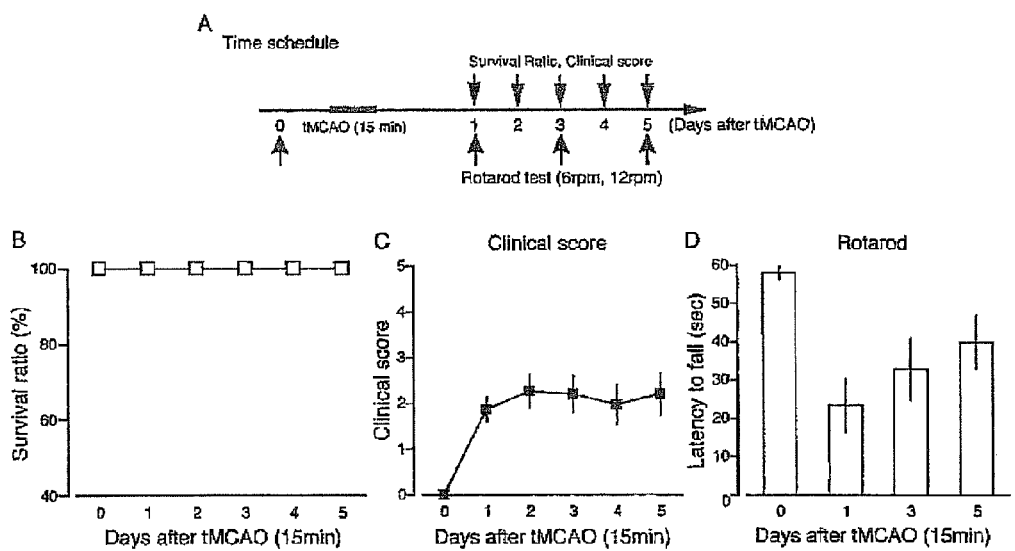
FIG. 2 shows the pathology of WT mouse after a 15-min treatment to produce transient Middle Cerebral Artery Occlusion (tMCAO). A: treatment to produce tMCAO of WT mouse and time schedule of performing test, B: survival ratio of WT mouse, C: clinical score of WT mouse, D: dwelling time of WT mouse on Rotarod (6 rpm).
Figure 3:
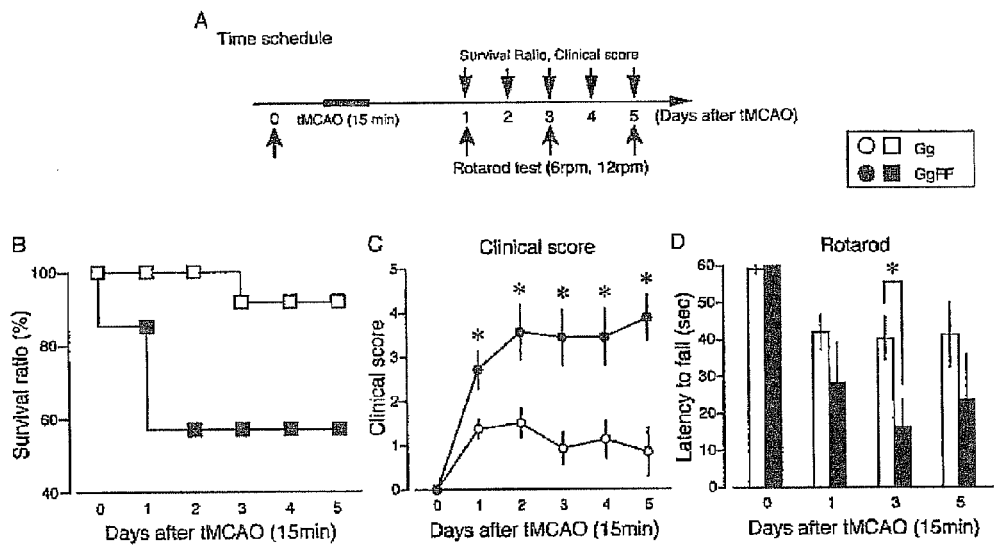
FIG. 3 shows the pathology of Gg mouse and GgFF mouse after a 15-min treatment to produce transient Middle Cerebral Artery Occlusion (tMCAO). * is a significant difference (p<0.05, Gg vs GgFF). A: time schedule of treatment to produce tMCAO and performing test of Gg mouse and GgFF mouse, B: survival ratio of Gg mouse and GgFF mouse, C: clinical score of Gg mouse and GgFF mouse, D: dwelling time of Gg mouse and GgFF mouse on Rotarod (6 rpm).

The left-middle cerebral artery was obstructed for 15 min in 8- to 16-week-old WT, Gg and GgFF mice, and the pathology of the mild cerebral apoplexy model having induced transient cerebral ischemia condition was evaluated (FIGS. 2, 3). Gg mice were used as a control group of the GgFF mice.

As a result of the evaluation with time of the survival ratio of the transient middle cerebral artery obstruction model after a treatment to produce tMCAO, the survival ratio of the WT mice did not change for 5 days (FIG. 2B). The Gg mice showed a survival ratio of not less than 90% on Day 4 (FIG. 3B). However, the GgFF mice showed a drastically decreased survival ratio, and the survival ratio already decreased to not more than 60% on day 2 after the treatment (FIG. 3B). The survival ratio (%) shows the survival ratio in percentage with the lapse of days based on the value measured before tMCAO as 100%.

In addition, the motility dysfunction of the transient middle cerebral artery obstruction model after the treatment to produce tMCAO was evaluated with the lapse of days. As a result, the WT mice and Gg mice showed only a weak motility disturbance (FIGS. 2C, 3C). However, the GgFF mice showed a disorder up to 4 points (FIG. 3C). In Examples of the present application, the clinical scores are shown by the following clinical scores 1-5. 1: paralysis of right forepaw, 2: unidirectional movement, 3: tilting to one direction by failure to keep balance, 4: disappearance of spontaneous movement, 5: death.

Furthermore, the motility function of the transient middle cerebral artery obstruction model after the treatment to produce tMCAO was evaluated with the lapse of days. As a result, the GgFF mice tended to shorten the dwelling time as compared to the Gg mice (FIG. 3D). The rotating speed of Rotarod was 6 rpm which is applicable to the cerebral apoplexy pathology model mouse.

Example 3

Figure 4:
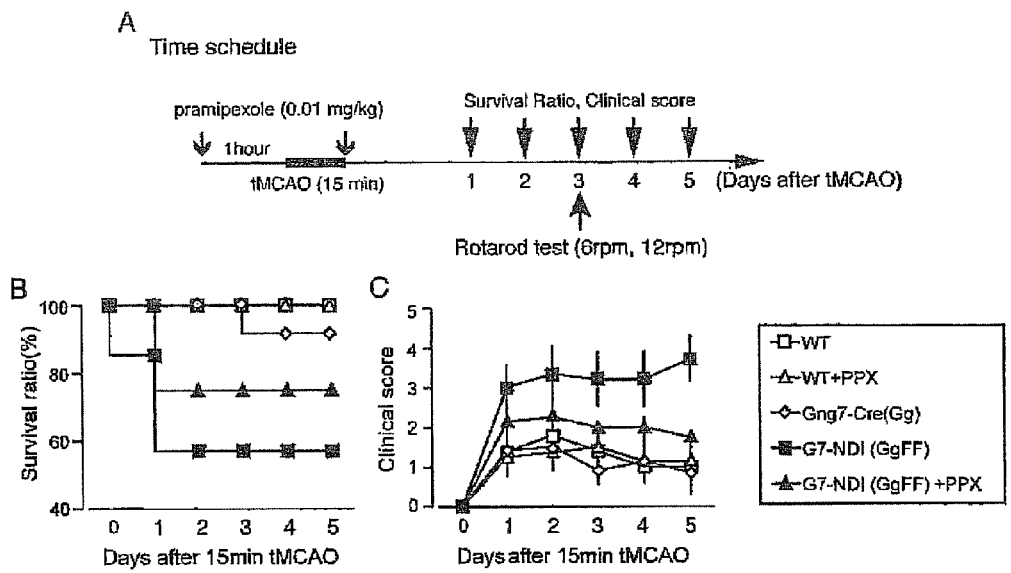
FIG. 4 shows the pathology of various mice administered with pramipexole, and after a 15-min treatment to produce transient Middle Cerebral Artery Occlusion (tMCAO). A: time schedule of pramipexole administration, treatment to produce tMCAO and performing test of various mice, B: survival ratio of various mice, C: clinical score of various mice.
Figure 5:
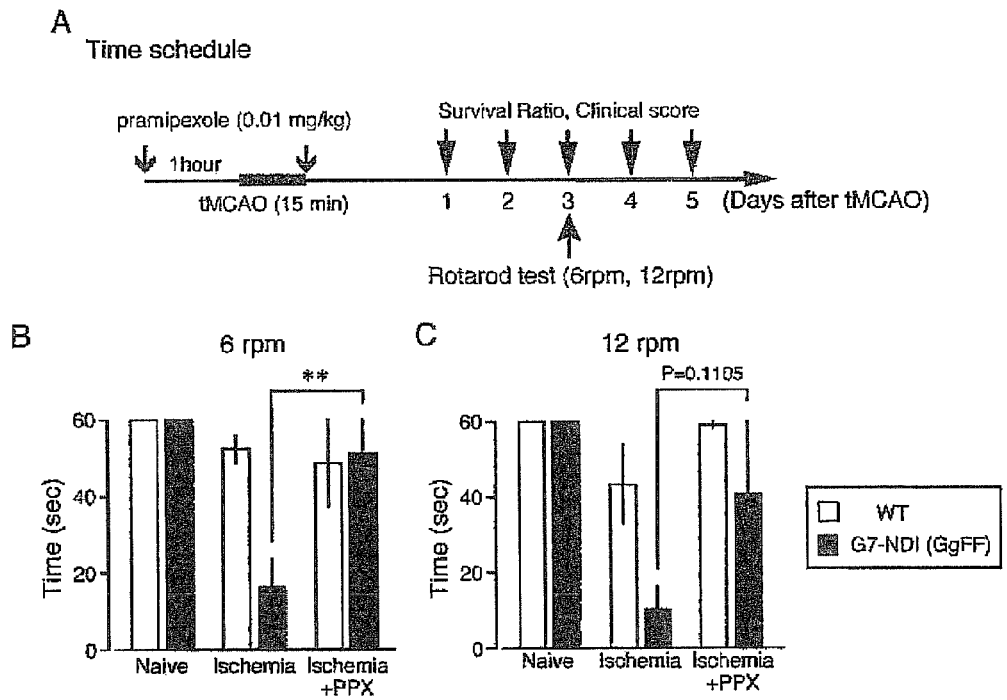
FIG. 5 shows the pathology of WT mouse and GgFF mouse administered with pramipexole and after a 15-min treatment to produce transient Middle Cerebral Artery Occlusion (tMCAO). ** is a significant difference (p<0.01, ischemia vs ischemia+PPX). A: time schedule of pramipexole administration, treatment to produce tMCAO and performing test of WT mouse and GgFF mouse, B: dwelling time of WT mouse and GgFF mouse on Rotarod (6 rpm), C: dwelling time of WT mouse and GgFF mouse on Rotarod (12 rpm).

Symptom Improving Effect of Dopamine D2 Receptor Agonist on Pathology of Young Mouse Deficient in Prothymosin α in Striatum Due to Ischemia In the same manner as in Example 2, the left-middle cerebral artery was obstructed for 15 min in 8- to 16-week-old WT, Gg and GgFF mice, and the improving effects of pramipexole on the survival ratio and motility dysfunction in the mild cerebral apoplexy model with the induced transient cerebral ischemia were evaluated (FIGS. 4, 5). Pramipexole (0.01 mg/kg) was intraperitoneally administered to the GgFF mice after 15-min tMCAO treatment, and the symptom improving effect was observed with time. The results are shown in survival ratio, Clinical score and Latency to fall. As the control group, the WT mice and Gg mice after the 15-min treatment to produce tMCAO in the same manner were used. PPX shows pramipexole.

As a result, while the WT mice did not show a difference between the administration group and the non-administration group, the GgFF mice showed a survival ratio improved to 75% in the administration group (FIG. 4B). In addition, the motility dysfunction was remarkably improved in the administration group of the GgFF mice (FIG. 5C). Furthermore, as for the motility function, the GgFF mice showed decreased motility function as compared to the WT mice under both conditions of 6 rpm and 12 rpm; however, intraperitoneal administration of pramipexole showed an improvement (FIGS. 5B, C).

Example 4

Figure 6:
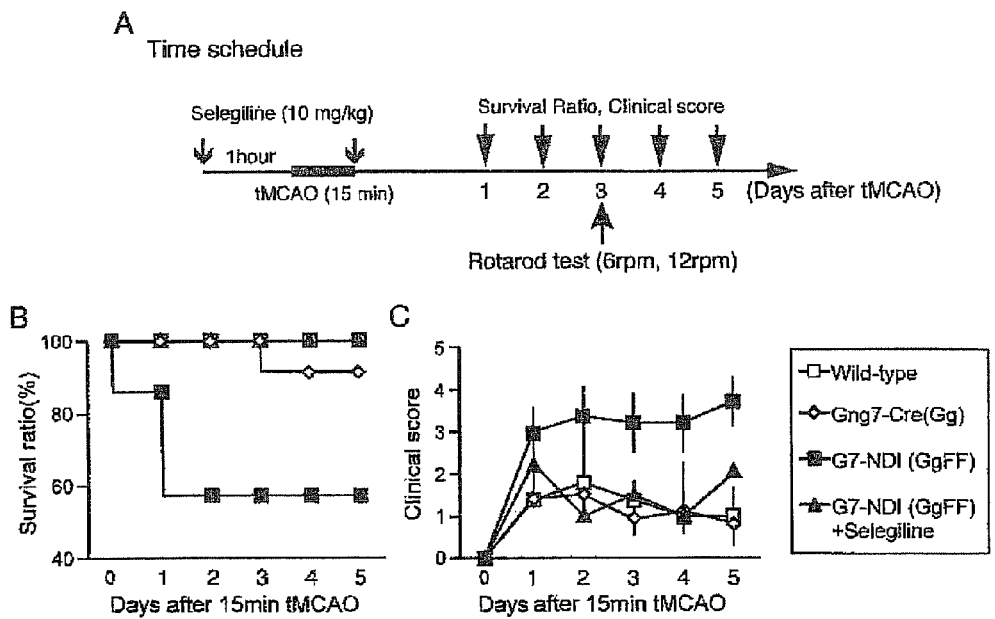
FIG. 6 shows the pathology of various mice administered with selegiline and after a 15-min treatment to produce transient Middle Cerebral Artery Occlusion (tMCAO). A: time schedule of selegiline administration, treatment to produce tMCAO and performing test of various mice, B: survival ratio of various mice, C: clinical score of various mice.
Figure 7:
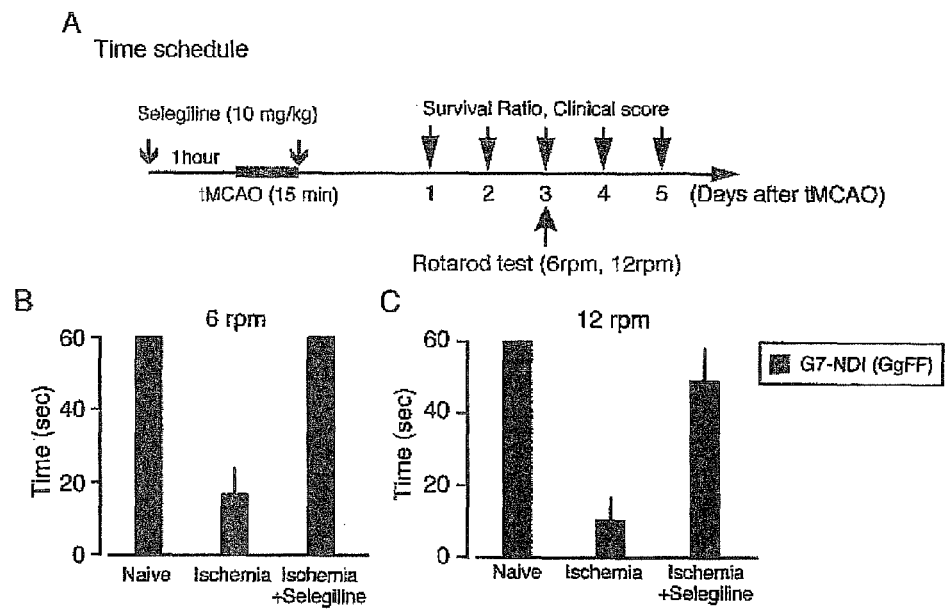
FIG. 7 shows the pathology of GgFF mouse administered with selegiline and after a 15-min treatment to produce transient Middle Cerebral Artery Occlusion (tMCAO). A: time schedule of selegiline administration, treatment to produce tMCAO and performing test of GgFF mouse, B: dwelling time of GgFF mouse on Rotarod (6 rpm), C: dwelling time of GgFF mouse on Rotarod (12 rpm).

Symptom Improving Effect of Selegiline on Pathology of Young Mouse Deficient in Prothymosin α in Striatum Due to Ischemia In the same manner as in Example 2, the left-middle cerebral artery was obstructed for 15 min in 8- to 16-week-old WT, Gg and GgFF mice, and the improving effects of selegiline on the survival ratio and motility dysfunction in the mild cerebral apoplexy model with the induced transient cerebral ischemia were evaluated (FIGS. 6, 7). Selegiline (10 mg/kg) was intraperitoneally administered to the GgFF mice after 15-min tMCAO treatment, and the symptom improving effect was observed with time. The results are shown in survival ratio, Clinical score and Latency to fall. As the control group, the WT mice and Gg mice after the 15-min treatment to produce tMCAO in the same manner were used.

As a result, the GgFF mice showed a markedly-improved survival ratio in the administration group (FIG. 6B). In addition, the motility dysfunction was remarkably improved in the administration group of the GgFF mice (FIG. 6C). Furthermore, as for the motility function, the GgFF mice showed improved motility function as compared to the non-administration group under both conditions of 6 rpm and 12 rpm by intraperitoneal administration of selegiline (FIGS. 7B, C).

In the above-mentioned Examples, the present inventors mainly analyzed 8- to 16-week-old young mice as the target. Thus, they also analyzed aged mice with weeks of age.

Example 5

Figure 8:
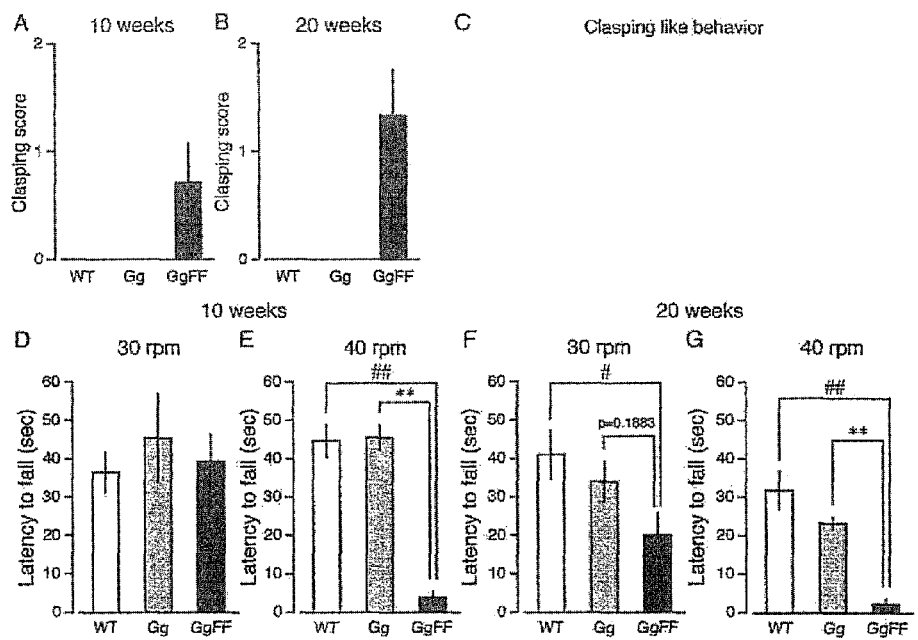
FIG. 8 shows clasping score and dwelling time on Rotarod of WT mouse, Gg mouse and GgFF mouse. ** is a significant difference (p<0.01, Gg vs GgFF), # is (p<0.05, WT vs GgFF), ## is (p<0.05, WT vs GgFF). A: clasping score of various 10-week-old mice, B: clasping score of various 20-week-old mice, C: photographs of clasping reflex of various mice, D: dwelling time of various 10-week-old mice on Rotarod (30 rpm), E: dwelling time of various 10-week-old mice on Rotarod (40 rpm), F: dwelling time of various 20-week-old mice on Rotarod (30 rpm), G: dwelling time of various 20-week-old mice on Rotarod (40 rpm).

Progression of Week Age-Dependent Clasping Reflex Behavior or Decrease in Motility Function of Mouse Deficient in Prothymosin α in Striatum The development of week age-dependent clasping reflex symptom and a decrease in the motility function were evaluated in the mice deficient in prothymosin α specifically to the striatum region of the basal nucleus (FIG. 8). The clasping scores were: no abnormality 0, behavior to clasp with forepaws or hindpaws 1, and behavior to clasp with and hold the forepaws and hindpaws 2. As a result, while the WT mice and Gg mice could not be confirmed to show abnormality, the clasping scores of the 10- and 20-week-old GgFF mice could be confirmed to be significantly high (FIGS. 8A, B, C).

In addition, for evaluation of the motility function, the mice were walked on a rotary rod, and the time of dwelling on the rod was measured (Rotarod method). Since control of each part of the whole body to take balance is necessary to walk on the rod, this test is used as an evaluation method of motor coordination. The test was performed under the conditions of Rotarod for mouse (MK-610A; Muromachi Kikai Co., Ltd.); maximum dwelling time 60 seconds, rod rotation speed 30 rpm and 40 rpm.

Before performing this test in this Example, a training trial was performed for 60 seconds at a rotating speed of 20 rpm successively 4 times per day at 1-hr intervals for 3 days. The 30 rpm means Rotarod rotating speed of 30 times rotation per min, and 40 rpm means 40 times rotation per min. As a result, it could be confirmed that the dwelling time of the GgFF mice on the Rotarod is significantly short as compared to that of the WT mice and Gg mice (FIGS. 8D, E).

Example 6

Figure 9:
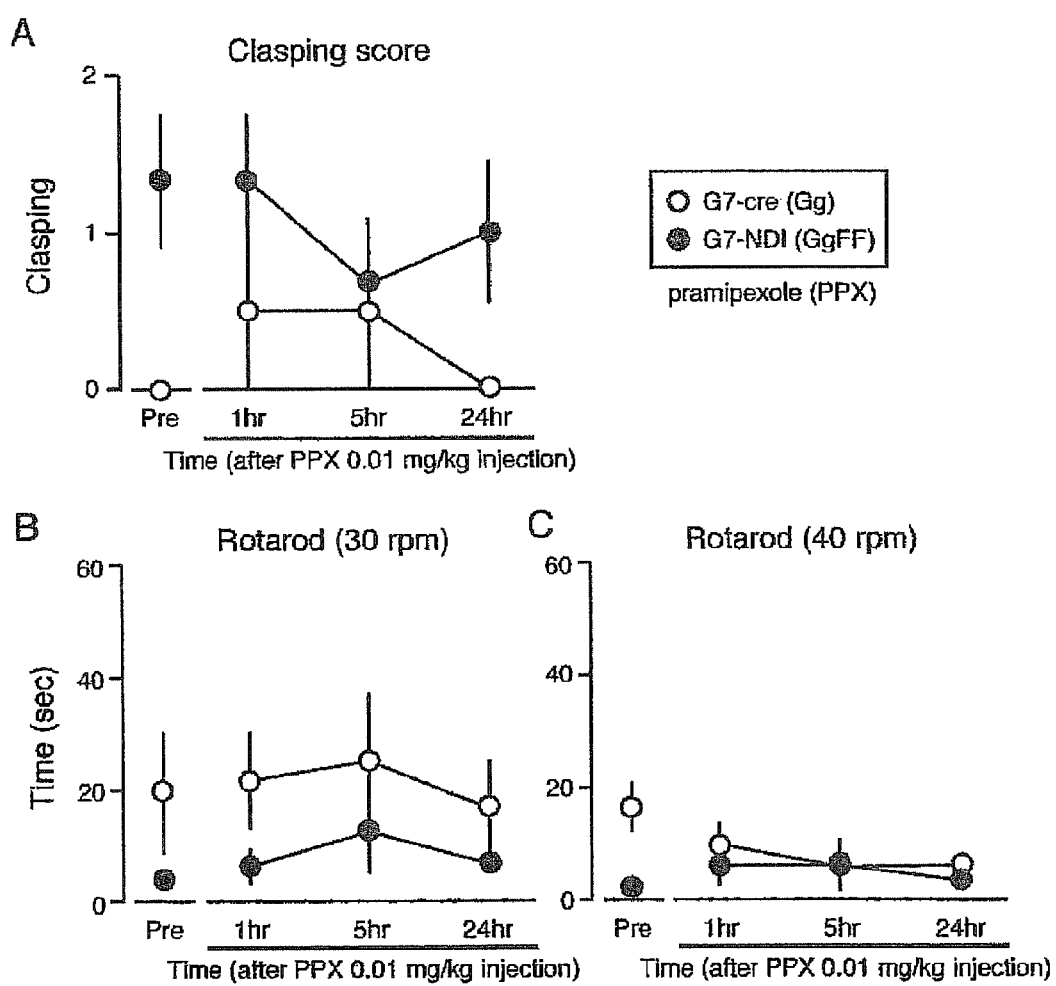
FIG. 9 shows clasping score and dwelling time on Rotarod of Gg mouse and GgFF mouse, within 24 hr after pramipexole administration. A: clasping score of Gg mouse and GgFF mouse, B: dwelling time of Gg mouse and GgFF mouse on Rotarod (30 rpm), C: dwelling time of Gg mouse and GgFF mouse on Rotarod (40 rpm).

Symptom Improving Effect of Dopamine D2 Receptor Agonist on Clasping Reflex Behavior or Decrease in Motility Function of Aged Mouse Deficient in Prothymosin α in Striatum Pramipexole (0.01 mg/kg), which is a dopamine D2 receptor agonist, was intraperitoneally administered to the GgFF mice showing clasping reflex and a decrease in the motility function and Gg mice as a control, and acute (within 24 hr) symptom improving effect was evaluated (FIG. 9). Pre shows before pramipexole administration, 1 hr shows 1 hr after the pramipexole administration, and 5 hr shows 5 hr later, and 24 hr shows 24 hr later. Pramipexole used in this Example of the present application was obtained by pulverizing pramipexole hydrochloride (bi-sifrol 0.125 mg tablet, Japan Boehringer Ingelheim) using a muddler and a mortar, dissolving same in saline, and adjusting to pH 7.0 with an aqueous sodium hydroxide solution before use. The solution was intraperitoneally administered to various mice with a 27-gauge injection needle. Five hours from the administration, the above-mentioned symptoms of the GgFF mice tended to be mitigated.

Figure 10:
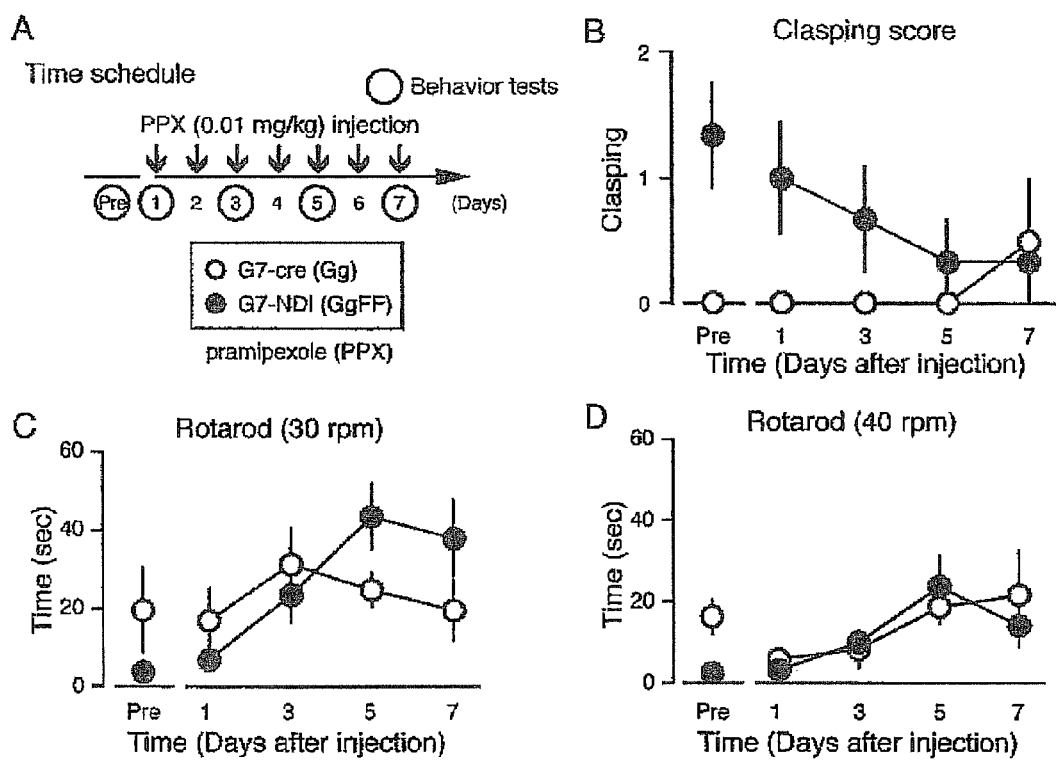
FIG. 10 shows clasping score and dwelling time on Rotarod of WT mouse, Gg mouse and GgFF mouse up to day 7 after pramipexole administration. A: time schedule of pramipexole administration and performing test of Gg mouse and GgFF mouse, B: clasping score of Gg mouse and GgFF mouse, C: dwelling time of Gg mouse and GgFF mouse on Rotarod (30 rpm), D: dwelling time of Gg mouse and GgFF mouse on Rotarod (40 rpm).

Also, pramipexole (0.01 mg/kg) was intraperitoneally administered chronically to the GgFF mice and Gg mice, and the symptom improving effect was evaluated principally according to the above-mentioned method except the administration method of pramipexole (FIG. 10). The Pre value is a measurement value before pramipexole administration. Pramipexole was administered every day from Day 1 to Day 7, and the value for Day 1 was measured 24 hr after the administration. Thereafter, the clasping scores were measured and motility function was evaluated by Rotarod every other day up to Day 7 (FIG. 10A). As a result, it could be confirmed that the clasping scores of the GgFF mice tended to improve with the lapse of days as compared to those before administration (FIG. 10B). In addition, it could be confirmed that the dwelling time of the GgFF mice on the Rotarod tended to be long with the lapse of days as compared to that before administration (FIGS. 10C, D).

Example 7

Figure 11:
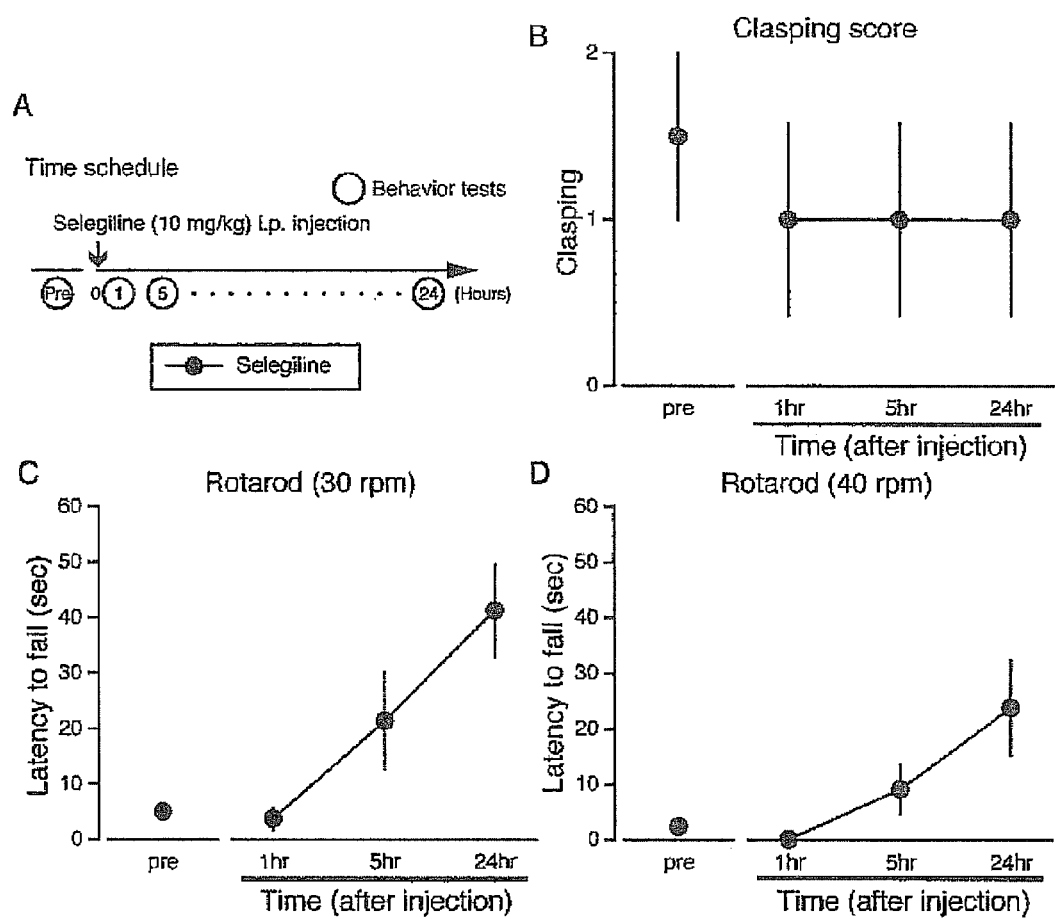
FIG. 11 shows clasping score and dwelling time on Rotarod of GgFF mouse within 24 hr after selegiline administration. A: time schedule of selegiline administration and performing test of GgFF mouse, B: clasping score of GgFF mouse, C: dwelling time of GgFF mouse on Rotarod (30 rpm), D: dwelling time of GgFF mouse on Rotarod (40 rpm).

Symptom Improving Effect of Selegiline on Clasping Reflex Behavior or Decrease in Motility Function of Aged Mouse Deficient in Prothymosin α in Striatum Selegiline (10 mg/kg), which is an MAO-B inhibitor relating to dopamine metabolism, was intraperitoneally administered to the GgFF mice, and acute (within 24 hr) symptom improving effect was evaluated (FIG. 11). Selegiline is one of the monoamineoxidase inhibitors (MAOI) and is a medicament that consequently increases the intracerebral dopamine level by selectively inhibiting MAO-B to prevent decomposition of dopamine. Pre shows before selegiline administration, 1 hr shows 1 hr after the selegiline administration, and 5 hr shows hr later, and 24 hr shows 24 hr later. As a result, it could be confirmed that the clasping scores of the GgFF mice tended to improve with the lapse of days as compared to those before administration (FIG. 11B). In addition, it could be confirmed that the dwelling time of the GgFF mice on the Rotarod tended to be long with the lapse of time as compared to that before administration (FIGS. 11C, D).

Example 8

Figure 12:
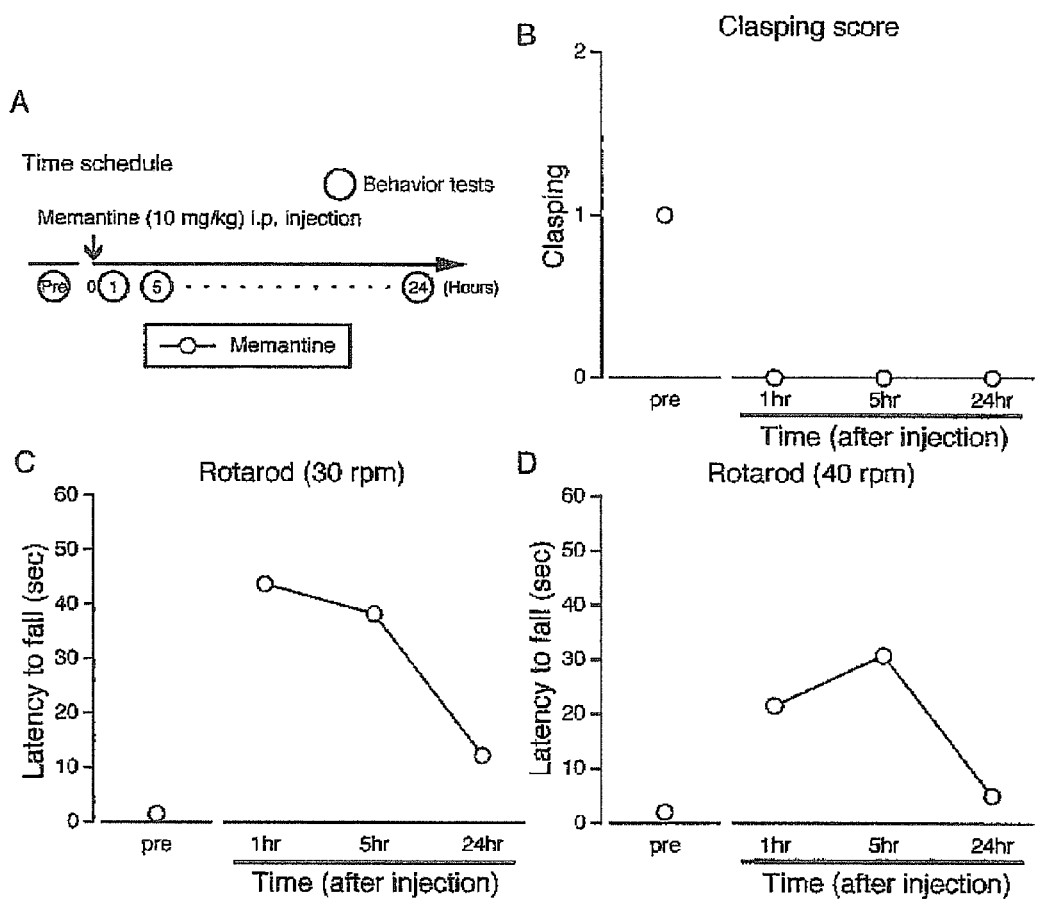
FIG. 12 shows clasping score and dwelling time on Rotarod of GgFF mouse within 24 hr after memantine administration. A: time schedule of memantine administration and performing test of GgFF mouse, B: clasping score of GgFF mouse, C: dwelling time of GgFF mouse on Rotarod (30 rpm), D: dwelling time of GgFF mouse on Rotarod (40 rpm).

Symptom Improving Effect of Memantine on Clasping Reflex Behavior or Decrease in Motility Function of Aged Mouse Deficient in Prothymosin α in Striatum Memantine (10 mg/kg) having an NMDA receptor antagonistic action suppressing cell death due to excess glutamic acid was intraperitoneally administered to the GgFF mice, and acute (within 24 hr) symptom improving effect was evaluated (FIG. 12). Pre shows before memantine administration, 1 hr shows 1 hr after the memantine administration, and 5 hr shows 5 hr later, and 24 hr shows 24 hr later. The motility function of the GgFF mice was most recovered 24 hr after the administration.

The symptom improving effect when memantine (10 mg/kg) was intraperitoneally administered chronically to the GgFF mice is shown. The Pre value is a measurement value before memantine administration. Memantine was administered every day from Day 1 to Day 7, and the value for Day 1 was measured 24 hr after the administration. Thereafter, the clasping scores were measured and motility function was evaluated by Rotarod every other day up to Day 7 (FIG. 13A). As a result, remarkable recovery of the symptom by chronic administration could be confirmed.

Example 9

Genotyping of Prothymosin α Deficient Aged Mouse

Figures 13, 14:
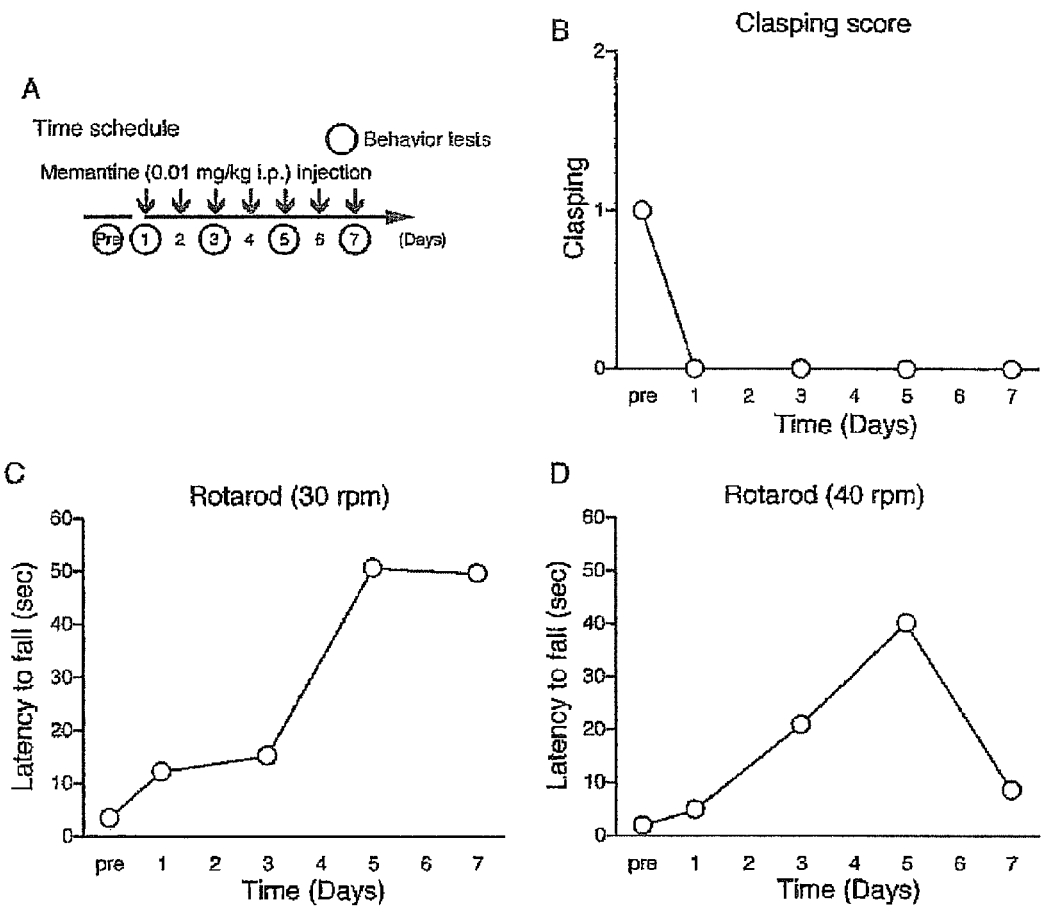
FIG. 13 shows clasping score and dwelling time on Rotarod of GgFF mouse up to day 7 after memantine administration. A: time schedule of memantine administration and performing test of GgFF mouse, B: clasping score of GgFF mouse, C: dwelling time of GgFF mouse on Rotarod (30 rpm), D: dwelling time of GgFF mouse on Rotarod (40 rpm).
FIG. 14 shows electrophoresis of genomic PCR product using GgFF mouse-derived genome as a template.

Ear sections of 20- to 30-week-old GgFF and Gg were placed in a 50 µl Extraction buffer (20×SSC 500 µl, 500 mM Tris-HCL pH 8.0 200 µl, 500 mM EDTA pH 8.0 400 µl, 10% SDS 1.0 ml, 1 mg/ml Proteinase K 500 µl, DW 7.4 ml), and the mixture was incubate overnight at 60° C. to extract DNA. Using MangoMix 2× master mix (BIOLINE), genotype was determined by the PCR method (FIG. 14). The primer and PCR conditions used were as follows.

```
GgFF;
5'-TCCTTGGCTTTTACTGCCAGAAG-3'    (SEQ ID NO: 1)

5'-TCACCTGGAGAATCAATCAAGGC-3'    (SEQ ID NO: 2)
```

94° C. 180s→94° C. 30s→60° C. 30s→72° C. 30s→72° C. 300s→4° C.∞(40 cycles of underlined parts)

```
Gg;
5'-GGCGACGTTGTTAGTACCTGAC-3'     (SEQ ID NO: 3)

5'-ATCCCTGAACATGTCCATCAGGTTC-3'  (SEQ ID NO: 4)

5'-TATAGGTACCCAGAAGTGAATTCGGTTCGC-3' (SEQ ID NO: 5)
```

95° C. 120s→95° C. 30s→60° C. 20s→72° C. 30s→72° C. 300s→4° C.∞(35cycle of underlined parts)

Example 10

Prothymosin α-Deficient Region of Prothymosin α-Deficient Aged Mouse

Under pentobarbital anesthesia, laparotomy and thoracotomy were performed on 20- to 30-week-old GgFF mice or Gg mice, the right atrial appendage of the heart was slit, $K^+$ free PBS was perfused from the left ventricle to remove blood, and 4% para-formaldehyde/0.1M PB was used for perfusion fixation. The brain was isolated, immersed in 25% sucrose/$K^+$ free PBS, and left standing at 4° C. overnight. The brain was embedded in O.C.T. compound (Sakura), and the tissue was rapidly frozen with ethanol/dry ice. Using Cryostat (CM1900, leica microsystems inc), a 30-µm thick brain section was produced. The tissue section was washed with PBST (0.1% TritonX-100 in $K^+$ free PBS), which was changed to 1% $H_2O_2$ for 30 min to decompose endogenous peroxidase. After washing with PBST (no indication of PBST washing in each step hereafter), the section was reacted in 2% BSA/2% anti-mouse serum (cappel 55435, MP Biomedicals)/PBST solution as a blocking reaction at room temperature for 1 hr. The section was incubated with anti-prothymosin α antibody (NT 2F11, ALEXIS Enzo Life Sciences) diluted to 1:1000 with 1% BSA/PBST solution at 4° C. overnight, and substituted to Biotinylated α-mouse IgG (1:500 Zymax) in 1% BSA/PBST for 1 hr. Then, it was substituted to vectastain ABC solution (Solution A 15 µl, Solution B 15 µl in 1% BSA/PBST 2000 µl) produced 30 min earlier for 1 hr to strengthen the signal. DAB solution (20 mg/mL) was dissolved in PBS (10 ml), 1% $CoCl_2$ (250 µL) and 1% $NiSO_4$ (200 µL) were added by small amounts and mixed therein, added with 30% $H_2O_2$ (Wako, 3.3 µl) and the mixture was used to substitute the ABC solution for about 5 min. The section was put on a silane-coated slide glass (Matsunami Glass Ind., Ltd.), air-dried, dehydrated with alcohol, penetrated with xylene, enclosed in Permount (Fisher Chemicals), and observed with a fluorescence phase contrast microscope (BZ-8000, KEYENCE CORPORATION). During fluorescent staining, a 30 µm section was produced, washed with PEST, immerse in 50% MeOH for 10 min and 100% MeOH for 10 min, washed with PEST and a blocking reaction was performed. As a secondary antibody, it was reacted with alexa fluor 488 anti-mouse IgG (1:300 Molecular probe) in 1% BSA/PEST for 2 hr.

Figure 15:
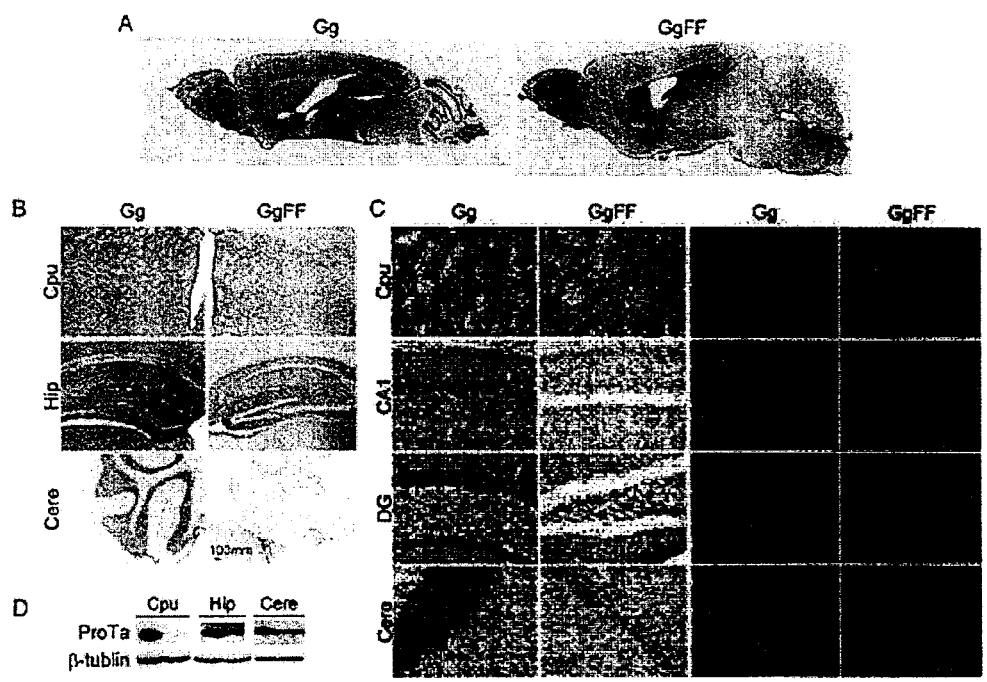
FIG. 15 shows a prothymosin α deficient region in the brains of Gg mouse and GgFF mouse. A: DAB-stained image of prothymosin α in the brain, B: 4× field of DAB-stained image of prothymosin α in the brain (Cpu; striatum, Hip; hippocampus, Cere; cerebellum), C: 20× field of DAB-stained image and fluorescent staining image of prothymosin α in the brain, D: Western blot image of prothymosin α.

The present inventors have heretofore confirmed by Real-time PCR that Gng7 is much expressed mainly in striatum, and also expressed in hippocampus and cerebellum. Using 30 µm brain sections of 20- to 30-week-old GgFF mice, immunohistochemistry of prothymosin α was performed to observe a remarkable decrease in the expression in striatum, hippocampus and cerebellum (FIG. 15 A, B). It was clarified from 20× field photographs of DAB staining and fluorescent staining that prothymosin α is absent in 70-80 percent of the cells of the striatum, the expression remains inside the dentate gyrus even in GgFF mice, prothymosin α expression remains in the Purkinje cell layer in the cerebellum, and prothymosin α is mainly deleted in the granular cell layer (FIG. 15C).

In addition, expression of prothymosin α in the striatum was confirmed by the immunoblot procedure. 20- to 30-week-old GgFF mice or Gg mice were decapitated, and the brain tissue of the mice was isolated on ice and washed with PBS. The brain tissue was sliced by a mouse brain slicer (Muromachi Kikai Co., Ltd.) in a 500 µm thickness, and each region of striatum, hippocampus and cerebellum was cut out with a razor, and placed in an Eppendorf tube containing 100 µl of SDS sample buffer (500 mM Tris-HCl (pH 6.8) 5 ml, 10% SDS 10 ml and 100% glycerol ml measured up with MQ to 50 ml). After disruption by ultrasonication by Bioruptor (Cosmo Bio) and centrifugation at 15000 rpm for 10 min, the supernatant was recovered and the protein was quantified using DC Protein Assay Regent (BIO-RAD laboratories). The protein (20 µg per lane) was electrophoresed on 15% SDS-PAGE at 30 mA, 300 V until the Dye reached the bottom of the gel. The protein in the gel was transcribed on to a nitrocellulose membrane by semi-dry method at 100 mA, 30 V for 90 min, followed by blocking with 5% skim milk, 2% Fetal bovine serum/TBST (TBS, 0.1% Tween20) for 1 hr. The primary antibody was diluted 1000-fold with the Buffer used for blocking and reacted overnight. After washing 3 times with TBST, HRP-labeled secondary antibody was diluted 2000-fold with the Buffer used for blocking and reacted for 2 hr. After washing 3 times with TBST, and the protein was chemically illuminated by Super Signal West Pico Chemiluminescent substrate and SuperSignal West Dura Extended Duration Substrate (Thermo scientific) and the signal was detected. As the primary antibody, anti-prothymosin α antibody (1:1000; ALEXIS) and anti-β-tubulin antibody (1:1000; Santa Cruz) were used, and as the secondary antibody, HRP-labeled anti mouse IgG antibody (1:2000; Promega) and HRP-labeled anti rabbit IgG antibody (1:2000; Promega) were used.

As a result, the expression of prothymosin α showed a decrease in striatum, hippocampus and cerebellum also by Western blot (FIG. 15D).

Example 11

Nerve Cell Form and Nerve Cell Number of Prothymosin α Deficient Aged Mouse

The present inventors have heretofore clarified both in vitro and in vivo that prothymosin α has an action to protect nerve cells in ischemia stress. Thus, whether the nerve cell form or cell number changed in the region where expression of prothymosin α decreased in the aforementioned GgFF mice in Example 10 was confirmed by Nissl staining. Nissl staining is used as a standard histological method to visualize nerve cells, wherein a Nissl substance composed of ribosomal RNA derived from the rough endoplasmic reticulum in the perikaryon and dendrite is stained. When a damage is done, it is redistributed in nerve cell and is also used as a marker of nerve cell death. In the same manner as in immunostaining, 30 μm brain section was produced, put on a silane-coated slide glass, air-dried, and washed with PBS. After immersion in MQ for about 10 seconds, it was immersed in cresyl violet solution (2.5 g cresylecht violet, 300 ml $H_2O$, 30 ml 1M NaOAc and 170 ml 1M AcOH were mixed and stirred in a stirrer for 7 days), which was warmed in a water bath to 37° C., for 15-30 min to allow for staining. After washing with MQ, it was dehydrated with alcohol, penetrated with xylene, enclosed in Permount, and observed with a microscope (Keyence).

Figure 16:
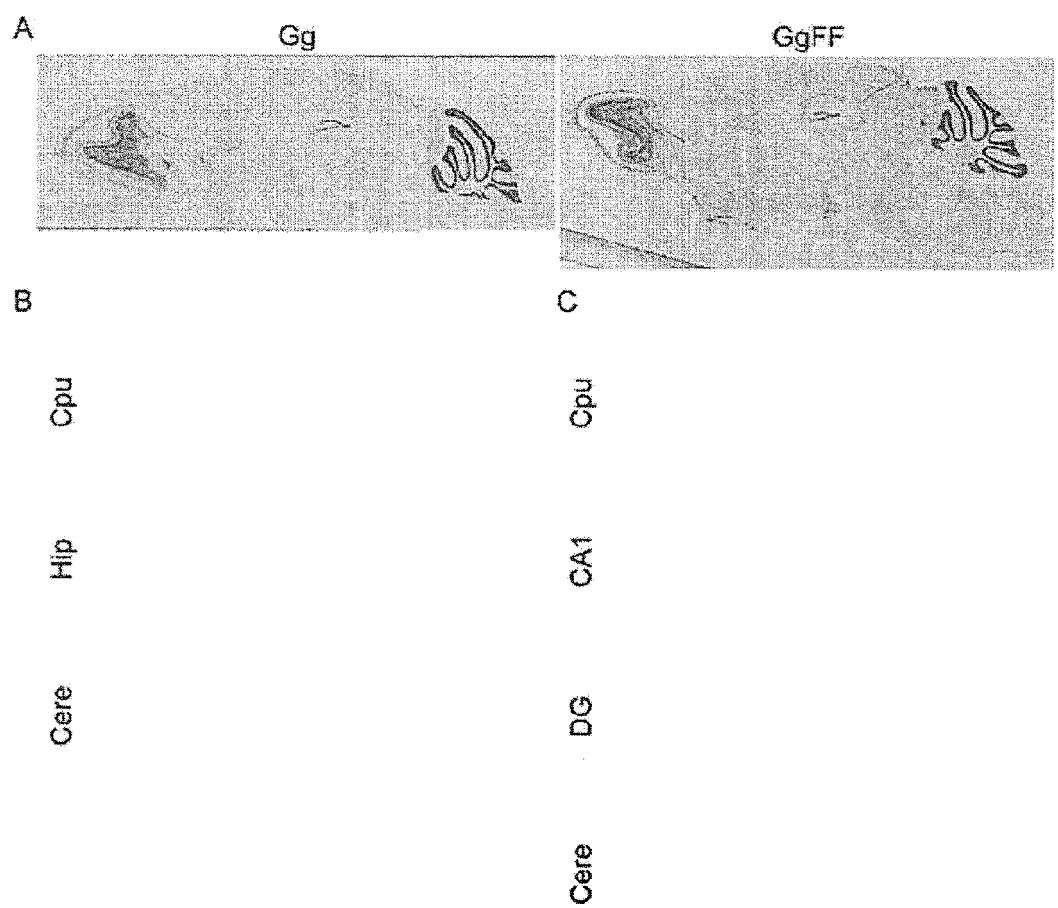
FIG. 16 shows changes in the nerve cell form and nerve cell number in the brains of Gg mouse and GgFF mouse. A: Nissl-stained image of the brain, B: 10× field of Nissl-stained image of the brain (Cpu; striatum, Hip; hippocampus, Cere; cerebellum), C: 20× field of Nissl-stained image of the brain (CA1; hippocampus CA1 region, DG; dentate gyrus).

As a result, remarkable nerve cell death or falling off, or disturbance in the arrangement of nerve cell layers in the striatum, hippocampus and cerebellum was not observed in the GgFF mice (FIG. 16 A, B, C).

Example 12

Figure 17:
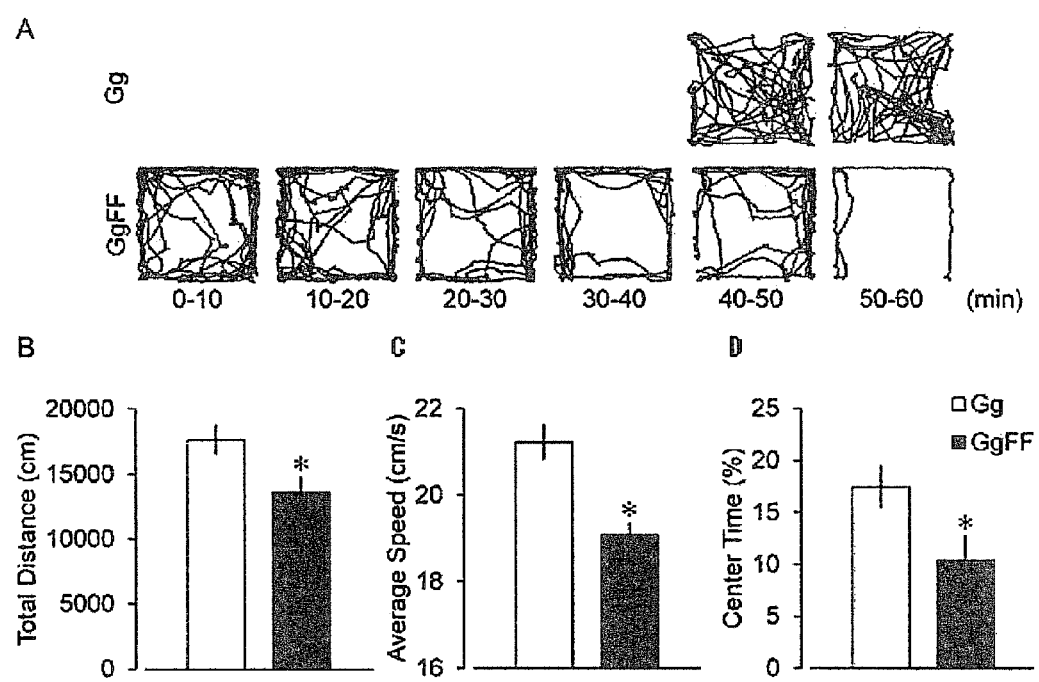
FIG. 17 shows evaluation of spontaneous motor activity and movement speed in Gg mouse and GgFF mouse. * is a significant difference (p<0.05, vs Gg). A: track of movement of mouse every 10 min in Open field test (representative mouse is shown as example), B: movement distance, C: average movement speed, D: center dwelling time.

Evaluation of Spontaneous Motor Activity and Movement Speed of Prothymosin α Deficient Aged Mouse Using 20-30-week-old mice, a spontaneous motility function under a novel environment was evaluated by an Open field test. The mouse was placed in an about 50lx room 30 min before the test to make the mouse adapted to the environment. The mouse was placed therein from a corner of an acrylic box (length 70 cm×width 70 cm×height 30 cm) and analyzed for 30 min by PC using a Video tracking system (Muromachi Kikai). The box was divided into 8×8 and the behavior time in the 4×4 center compartments was measured as an index of anxiety-like behavior. In the Open field test, the 20-30-week-old GgFF mice showed a remarkable decreased in the spontaneous motor activity (FIG. 17 A, B). In addition, the movement speed decreased and the center dwelling time was also shortened (FIG. 17 C, D).

These results have clarified that the GgFF mice showed age week-dependent motility dysfunction or promoted anxiety-like behavior.

Example 13

Evaluation of Anxiety-Like Symptom in Prothymosin α-Deficient Aged Mouse

Furthermore, to examine whether an anxiety-like behavior is enhanced, 20- to 30-week-old GgFF mice were subjected to a Marble burying test and a Novelty induced hypophagia test, which are tests for other anxiety behaviors.

Figure 18:
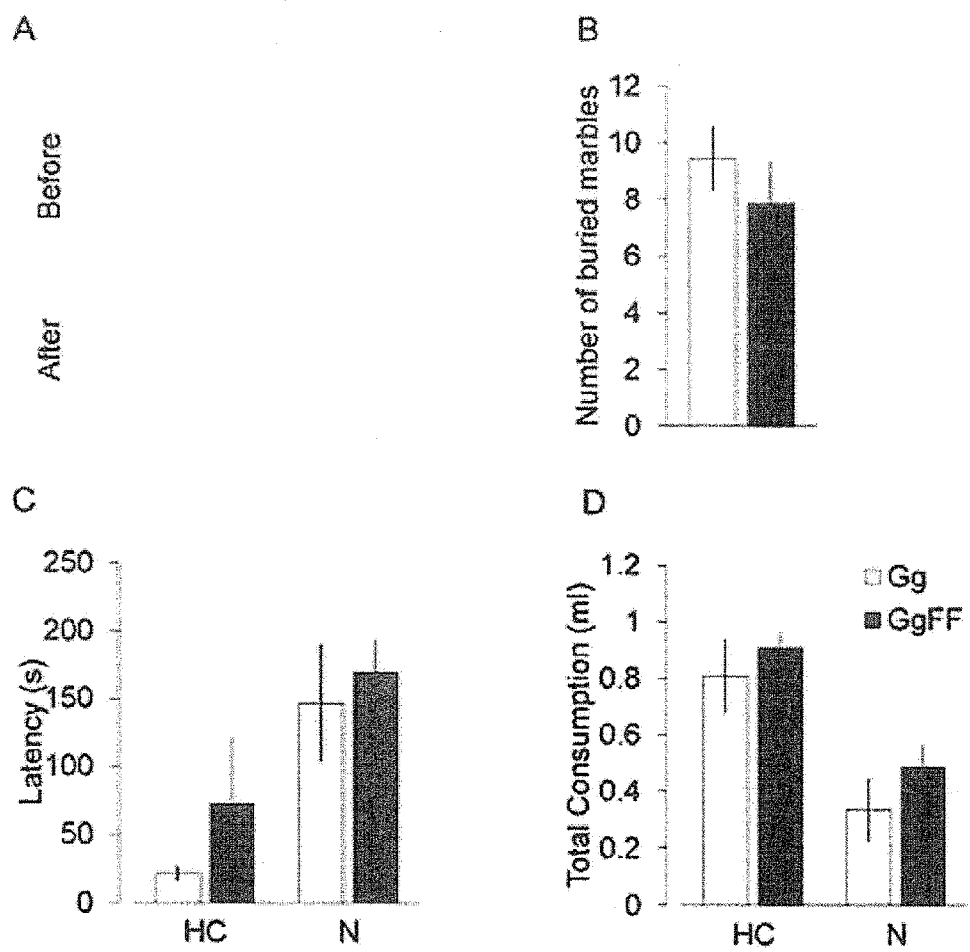
FIG. 18 shows evaluation of anxiety-like symptom in Gg mouse and GgFF mouse. A: beads before and after marble burying test, B: number of beads hidden by mouse in marble burying test, C: time before mouse goes to drink milk in novelty induced hypophagia test, D: amount of milk drunk by mouse in 30 min in novelty induced hypophagia test.

Marble burying test is being recognized as an anxiety-like behavior test related to obsessive disorders, since the behavior of a mouse to cover harmless glass beads with floor cover is apparently similar to a threatening act of obsessive-compulsive disorder patients who repeat the act while recognizing it to be unreasonable. It has been reported that the number of the beads hidden decreases by the administration of an anti-anxiety drug. A floor cover (5 cm) was placed in an acrylic box (length 28 cm×width 45 cm×height 20 cm) and 17 mm blue beads were put (5×5) thereon at an equal distance. The cage was put in a dim place, and the mouse was placed in the cage. After 30 min, the mouse is recovered, and the number of beads buried in the floor cover by ⅔ or more was counted. While the number of beads hidden by the GgFF mice in this test was not significant difference from that by the Gg mice, it was on a slight decrease tendency, and a decrease in the motility function was observed (FIG. 18 A, B).

In the Novelty induced hypophagia test, the time before the mice go to drink condensed milk and the amount of the milk drunk are compared between a group that drinks condensed milk in the Homecage (HC) and a group that drinks it in a novel environment (Novelty; N), based on which the anxiety behavior is evaluated. It is considered that a mouse with promoted anxiety behavior takes a longer time before going to drink milk in a novel environment and the amount drunk also decreases. First, the mice raised in a group were placed in a dim room of about 50lx and allowed to freely ingest 5 ml of 25% condensed milk. This was repeated once per day for 3 days to make them learn the taste of the milk. On day 4, the mice were divided into 2 groups of those capable of drinking milk in the Homecage in a dim room as in the 3 days (Homecage group) and those capable of drinking milk in a transparent cage without a floor cover and lighted up brightly at 1000lx (Novelty group), and the experiment was performed. One mouse from each group was tried for 30 min, and the time until it drank milk for the first time, and the amount of milk drunk every 5 min were measured. In this test, both the HC group and N group of GgFF mice showed no significant difference in the time until the mouse goes to drink milk and the amount of milk drunk (FIG. 18 C, D).

These results have clarified that the GgFF mice did not show promoted anxiety-like behavior.

Example 14

Evaluation of Motility Function in Prothymosin α Deficient Aged Mouse

In the previous tests, it was clarified that 20- to 30-week-old GgFF mice show a decrease in the spontaneous motor activity. Therefore, to examine the motility function of GgFF mice in more detail, a Rotarod test, further a Stationary thin rod test, and Footprint test were performed in the same manner as with young mouse.

Figure 19:
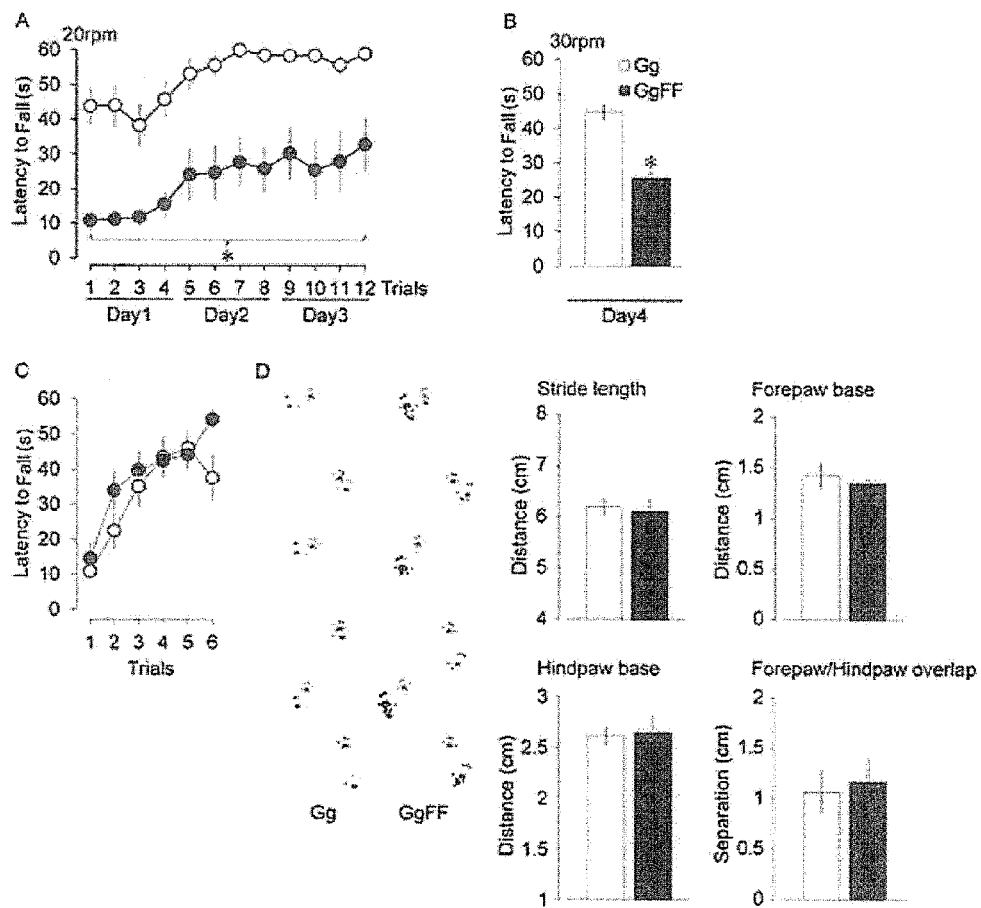
FIG. 19 shows evaluation of motility function of Gg mouse and GgFF mouse. * is a significant difference (p<0.05, vs Gg). A: dwelling time of mouse on Rotarod (20 rpm) for the first 3 days, B: dwelling time of mouse on Rotarod (30 rpm) on day 4, C: dwelling time on rod in stationary thin rod test, D: stride length of mouse in footprint test, distance between forepaws, distance between hindpaws and forepaw/hindpaw overlap.

In the Rotarod test, GgFF mice were remarkably fast in the time before falling off from a rotor, as compared to the Gg mice, from the first time of training to learn how to walk on the rotor rotating at a low speed of 20 rpm. While Although the GgFF mice showed a little achievement during the 3 days of training, they could not show motility function equivalent to that of Gg mice (FIG. 19 A). On day 4, the test was run at a higher speed of 30 rpm. Similar to the training results, the time before falling off from the rotor was short (FIG. 19 B).

Furthermore, to examine the sense of balance, a Stationary thin rod test was performed to examine the time before falling off from a thin, stopped rod. A 50 cm long smooth stainless rod (diameter 1.5 cm) was set horizontally at a height of 40 cm from the ground, the mouse was placed on the center of the rod to prevent injury, and the time before falling off was measured. The maximum dwelling time was set to seconds, 6 trials were performed at an interval of 1 hr. As a result, the GgFF mice, like the Gg mice, gradually came to be able to stay on the rod in 6 trials, and no significant difference was found (FIG. 19 C).

In addition, in a Footprint test to examine walking function, the sole of the forepaws and hindpaws of the mouse were painted with red ink and black ink, and the mouse was made to walk on a path (width 48 mm, length 650 mm, height 230 mm). In this case, utilizing the nature of the mouse to prefer a dark place, a light was flashed from behind to induce moving forward. The following parameters were analyzed with an average of 3 steps excluding the start of walking and the end of walking, and the walking function was evaluated. As a result, the GgFF mice did not show an abnormal walking manner, and no significant difference from the Gg mice was found in all items of walking width (Stride length: distance between one forepaw and the same forepaw, average of right and left), distance between forepaws (Forepaw base: distance between right and left forepaws), distance between hindpaws (Hindpaw base: distance between right and left hindpaws), fore-hindpaw overlap (Forepaw/Hindpaw overlap: distance between one forepaw and a hindpaw, average of right and left) (FIG. 19 D).

These results suggest that 20- to 30-week-old GgFF mice do not show marked motility dysfunction in, for example, normal walking and balancing, but show abnormality in high motor coordination as in the Rotarod test.

Example 15

Effect of Administration of D1, D2 Agonists on Motility Dysfunction of Prothymosin α Deficient Aged Mouse The earlier results have clarified that GgFF mice spontaneously develop motility dysfunction. Thus, whether the motility dysfunction of the GgFF mice can be treated with the dopamine agonists used for Parkinson's disease wherein the striatum is the pathology as in the GgFF mice was examined.

Figure 20:
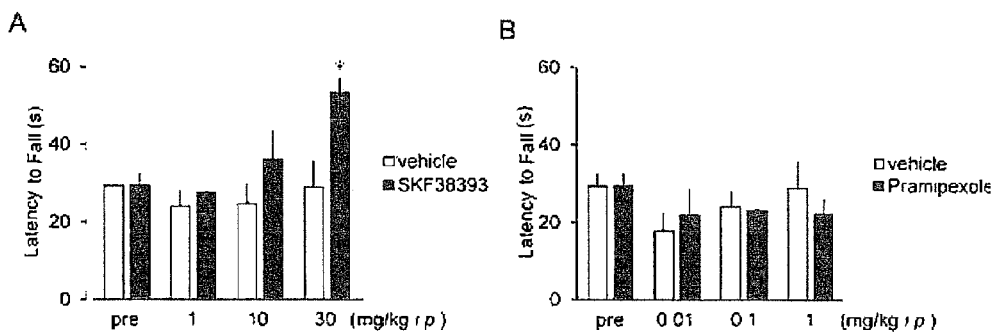
FIG. 20 shows the dwelling time of GgFF mouse on Rotarod in 5 hr after D1 agonist, D2 agonist administration. * is a significant difference (p<0.05, vs vehicle). A: dwelling time of GgFF mouse on Rotarod (30 rpm) after SKF38393 administration, B: dwelling time of GgFF mouse on Rotarod (30 rpm) after pramipexole administration.

After 5 hr from the intraperitoneal administration of 30 mg/kg of SKF38393, which is a D1 agonist, the motility dysfunction significantly improved in the Rotarod test (FIG. 20A). However, an improving effect was not observed by the administration of pramipexole, which is a D2 agonist D2, even at the maximum dose of 1 mg/kg (FIG. 20 B).

These results suggest that the deficiency of prothymosin α in Gng7 expressing cell exerts some influence on the balance of dopaminergic neuron.

Example 16

Behavioral Analysis of Prothymosin α Deficient Aged Mouse

Figure 21:
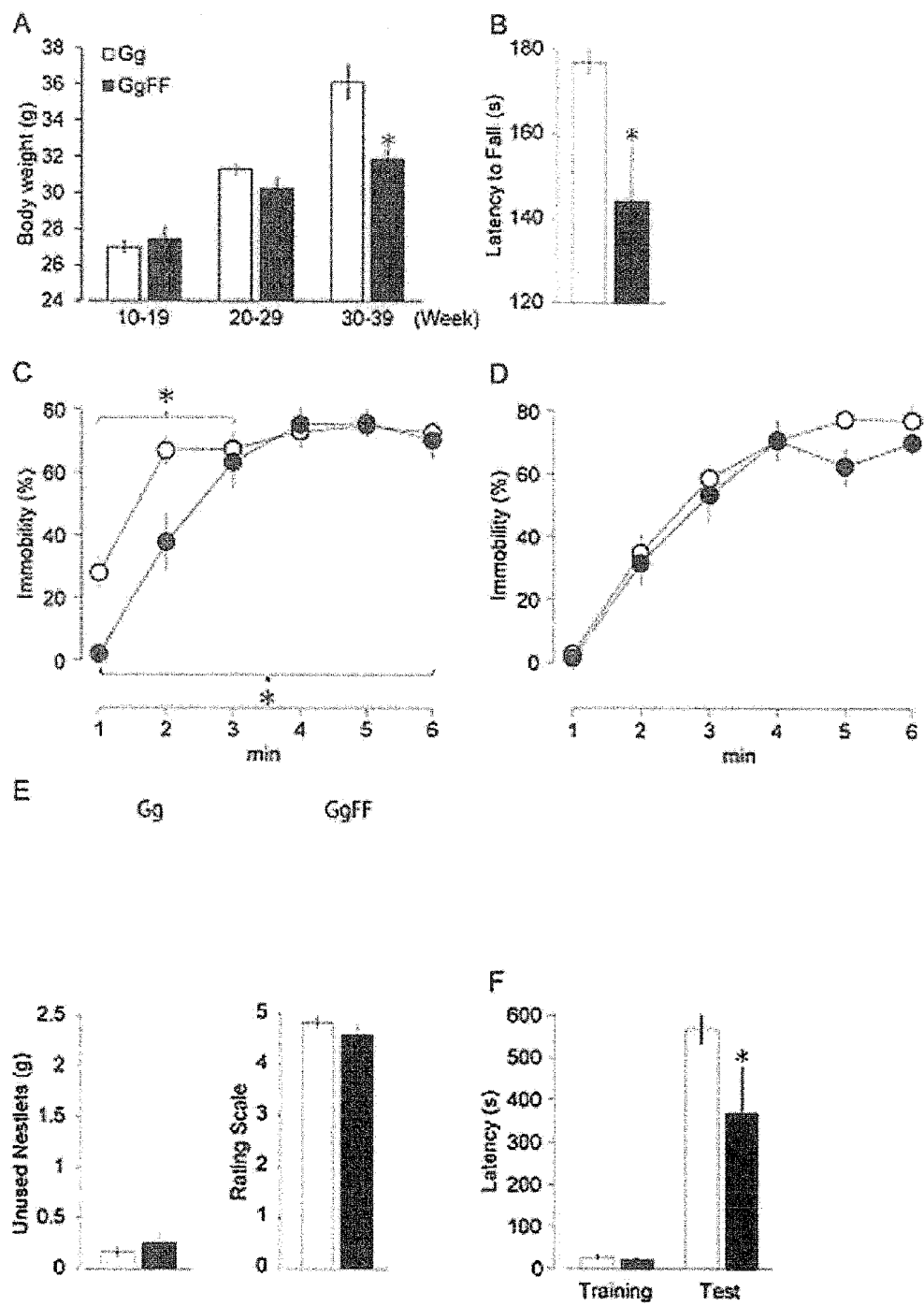
FIG. 21 shows other behavioral analysis results of Gg mouse and GgFF mouse. * is a significant difference (p<0.05, vs Gg). A: average body weight of mouse at every 10 weeks of age, B: time before falling off from net in wire hang test, C: ratio of immobility time of mouse per 1 min in tail suspension test, D: ratio of immobility time of mouse per 1 min in forced swim test, E: amount of unused Nestlets and score of nest shape after one night in nest building test, F: time before entering dark box in step through test, Training; day 1, Test; day 2.

Also, the GgFF mice were further verified for the following points.
(1) Body Weight
The body weight did not show a significant difference, but the level of body weight gain decreased as the weeks of age increased as compared to the control group. Up to 29 weeks of age, no difference was found from the Gg mice, but a significant decrease in the body weight was found at 39 weeks of age (FIG. 21A).
(2) Grasping Power
As an evaluation of muscle power, a Wirehang test was performed. A mouse was put on a 1 cm square lattice mesh, the mesh was fixed upside down at a height of 30 cm. The time before the mouse fell off was measured, setting the maximum to seconds. In the Wirehang test for measuring the grasping power, the Gg mice mostly did not fall for the maximum latent time of 180 seconds, but the GgFF mice fell about 20 seconds earlier (FIG. 21 B).
(3) Depression-Like Symptom
The depression-like symptom was evaluated by a Tail suspension test and a Porsolt forced swim test.

In the Tail suspension test, the tail of a mouse was fixed with a tape at the tip of a wooden rod, and the mouse was hung at a height of 30 cm. The time before becoming motionless and the motionless time per 1 min were measured for 6 min. As a result, the GgFF mice showed a significant decrease in the motionless time throughout the entire 6 min and the decrease was particularly remarkable in the first 3 min (FIG. 21 C).

In the Porsolt forced swim test, water at $25\pm1°$ C. was charged in an acrylic cylindrical container (diameter 20 cm height 30 cm) up to 20 cm. A mouse was placed in the container, and the time before becoming motionless and the motionless time per 1 min were measured for 6 min. After the measurement, the mouse was recovered, and dried with a Kim towel. As a result, no significant difference was found between the Gg mice and the GgFF mice (FIG. 21 D).
(4) Sociality
To examine consideration of the surrounding environment and sociality, a Nest building test was performed. At 19:00, which is one hour before the dark period of the light-dark cycle (light period 8:00-20:00/dark period 20:00-8:00), the mice were individually placed in a large cage, and Nestlet (2.5 g) (Ancare) was placed therein. The shape of the nest was scored the next morning based on the following criteria, and the amount of Nestlet not used was measured.
Score 1. 90% of Nestlet is not used.
Score 2. 50-90% of Nestlet is not used.
Score 3. 50% or more of Nestlet is used. 90% or more of Nestlet is not gathered in the corner. No nest-like material is found.
Score 4. 90% or more of Nestlet is used, and gathered in the corner. A flat nest is found.
Score 5. 90% or more of Nestlet is used, and a complete nest with a dent is found.

As a result, it was clarified that the GgFF mice and the Gg mice were not different in the amount of Nestlets not used as a nest and scoring of the nest shape, and they do not have social abnormality (FIG. 21 E).
(5) Learning Function
A Step through test was used for the evaluation of learning function. In the training on day 1 to let the Gg mice and GgFF mice learn about an electric current, they showed no significant difference. Therefore, the both groups are considered to have been conditioned in the same manner. However, in the test on day 2, the GgFF mice entered a dark box to be applied with an electric current faster than the Gg mice, whereby a decrease in the learning function was suggested (FIG. F).

INDUSTRIAL APPLICABILITY

Since the present invention has succeeded in the production of a non-human mammal deficient in the expression of prothymosin α gene in the striatum as a model mouse of neurodegenerative diseases including Huntington's disease, it can make a contribution to the study of the onset mechanism and the like of the diseases. In addition, the non-human mammal can be utilized for screening for a novel prophylactic/therapeutic drug for the diseases.

This application is based on a patent application No. 2011-119651 filed in Japan (filing date: May 27, 2011) and a patent application No. 2012-026636 filed in Japan (filing date: Feb. 9, 2012), the contents of which are incorporated in full herein.

The invention claimed is:

1. A mouse whose genome comprises (a) a cre gene whose expression is regulated by a G protein γ7 subunit gene promoter and (b) a homozygous prothymosin α gene flanked with loxP sequences, wherein the mouse is deficient in the expression of the prothymosin α gene in the striatum, and wherein the mouse, as compared to a corresponding wild-type mouse,
    (1) is vulnerable to cerebral ischemia produced by a treatment, wherein survival of the mouse with cerebral ischemia is decreased,
    (2) is inferior in motility,
    (3) spontaneously develops the conditions of the above-mentioned (1) and (2) by aging, and
    (4) shows improve symptoms of the above-mentioned (1), (2) and (3) by a dopamine D2 receptor agonist, a dopamine metabolism inhibitor, an N-methyl-D-aspartate (NMDA) receptor antagonist or a dopamine D1 receptor agonist.

2. The mouse according to claim 1, wherein the dopamine D2 receptor agonist is pramipexole, pergolide, cabergoline, talipexole or ropinirole.

3. The mouse according to claim 1, wherein the dopamine metabolism inhibitor is selegiline, entacapone, amantadine, L-3,4-dihydroxyphenylalanine (L-DOPA), droxidopa or zonisamide.

4. The mouse according to claim 1, wherein the NMDA receptor antagonist is memantine or CP-101606.

5. The mouse according to claim 1, wherein the dopamine D1 receptor agonist is SKF38393.

6. A screening method for a therapeutic/prophylactic drug for Huntington's disease or dystonia derived from an ischemic disease, comprising
applying a test compound to the mouse according to claim 1,
measuring (1) survival of the mouse in a cerebral ischemia produced by a treatment and/or (2) motility of the mouse, and
selecting a test compound that improves (1) survival of the mouse in cerebral ischemia produced by a treatment and/or (2) motility of the mouse as compared to the mouse according to claim 1 that has not been administered the test compound,
thereby identifying a therapeutic/prophylactic drug for Huntington's disease or dystopia derived from an ischemic disease.

7. The screening method according to claim 6, wherein the test compound is a dopamine D2 receptor agonist.

8. The screening method according to claim 6, wherein the test compound is a dopamine metabolism inhibitor.

9. The screening method according to claim 6, wherein the test compound is an NMDA receptor antagonist.

10. The screening method according to claim 6, wherein the test compound is a dopamine D1 receptor agonist.

11. A screening method for a therapeutic/prophylactic drug for Huntington's disease or dystonia derived from an ischemic disease, comprising
applying a test compound to the mouse according to claim 1, wherein the age of the mouse is 20-weeks-old or more,
measuring (1) survival of the mouse in a cerebral ischemia produced by a treatment and/or (2) motility of the mouse, and
selecting a test compound that improves (1) survival of the mouse in cerebral ischemia produced by a treatment and/or (2) motility of the mouse as compared to the mouse according to claim 1 that has not been administered the test compound,
thereby identifying a therapeutic/prophylactic drug for Huntington's disease or dystopia derived from an ischemic disease.

12. The screening method according to claim 11, wherein the test compound is a dopamine D2 receptor agonist.

13. The screening method according to claim 11, wherein the test compound is a dopamine metabolism inhibitor.

14. The screening method according to claim 11, wherein the test compound is an NMDA receptor antagonist.

15. The screening method according to claim 11, wherein the test compound is a dopamine D1 receptor agonist.

16. A screening method for an agent that reduces vulnerability to cerebral ischemia produced by a treatment or inferiority in motility comprising
applying a test compound to the mouse according to claim 1,
measuring (1) survival of the mouse in a cerebral ischemia produced by a treatment and/or (2) motility of the mouse, and
selecting a test compound that improves (1) survival of the mouse in cerebral ischemia produced by a treatment and/or (2) motility of the mouse as compared to the mouse according to claim 1 that has not been administered the test compound,
thereby identifying an agent that reduces vulnerability to cerebral ischemia produced by a treatment or inferiority in motility.

17. A screening method for an agent that reduces vulnerability to cerebral ischemia produced by a treatment or inferiority in motility comprising
applying a test compound to the mouse according to claim 1, wherein the age of the mouse is 20-weeks-old or more,
measuring (1) survival of the mouse in a cerebral ischemia produced by a treatment and/or (2) motility of the mouse, and
selecting a test compound that improves (1) survival of the mouse in cerebral ischemia produced by a treatment and/or (2) motility of the mouse as compared to the mouse according to claim 1 that has not been administered the test compound,
thereby identifying an agent that reduces vulnerability to cerebral ischemia produced by a treatment or inferiority in motility.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tccttggctt ttactgccag aag                                              23

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
tcacctggag aatcaatcaa ggc                                              23

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ggcgacgttg ttagtacctg ac                                               22

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
atccctgaac atgtccatca ggttc                                            25

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
tataggtacc cagaagtgaa ttcggttcgc                                       30
```